United States Patent
Guccione et al.

(10) Patent No.: US 11,136,579 B2
(45) Date of Patent: Oct. 5, 2021

(54) METHOD OF TREATING CANCER BY ANTISENSE OLIGONUCLEOTIDES TARGETING PRDM15

(71) Applicant: AGENCY FOR SCIENCE, TECHNOLOGY AND RESEARCH, Singapore (SG)

(72) Inventors: Ernesto Guccione, Singapore (SG); Keng Boon Dave Wee, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 0 days.

(21) Appl. No.: 16/329,970

(22) PCT Filed: Sep. 4, 2017

(86) PCT No.: PCT/SG2017/050436
§ 371 (c)(1),
(2) Date: Mar. 1, 2019

(87) PCT Pub. No.: WO2018/044239
PCT Pub. Date: Mar. 8, 2018

(65) Prior Publication Data
US 2020/0181612 A1 Jun. 11, 2020

(30) Foreign Application Priority Data
Sep. 1, 2016 (SG) ............................. 10201607303Y

(51) Int. Cl.
*C12N 15/11* (2006.01)
*C12N 15/113* (2010.01)
*A61P 35/00* (2006.01)
*A61K 9/127* (2006.01)

(52) U.S. Cl.
CPC ............ *C12N 15/113* (2013.01); *A61K 9/127* (2013.01); *A61P 35/00* (2018.01)

(58) Field of Classification Search
CPC ........ C12N 15/113; A61P 35/00; A61K 9/127
See application file for complete search history.

(56) References Cited

U.S. PATENT DOCUMENTS

2008/0050393 A1* 2/2008 Tang ...................... C07K 14/47
424/184.1

FOREIGN PATENT DOCUMENTS

| JP | 2013-100286 A | 5/2013 | | |
|---|---|---|---|---|
| WO | WO-9949065 A1 * | 9/1999 | ............ | A61P 17/06 |
| WO | 02/24906 A1 | 3/2002 | | |
| WO | 2007147613 A2 | 12/2007 | | |
| WO | WO-2011078797 A2 * | 6/2011 | ............ | C12N 15/113 |
| WO | 2012/092645 A1 | 7/2012 | | |
| WO | 2014070868 A1 | 5/2014 | | |
| WO | WO-2014187856 A1 * | 11/2014 | ............ | C12N 15/113 |
| WO | 2015085172 A2 | 6/2015 | | |

OTHER PUBLICATIONS

Communication (International Search Report and Written Opinion) issued by the International Searching Authority in International Application No. PCT/SG2017/050436 dated Nov. 3, 2017, 12 pages total.

Communication (International Preliminary Report on Patentability) issued by the International Searching Authority in International Application No. PCT/SG2017/050436 dated Jul. 20, 2018, 6 pages total.

Beck, K.M. et al., "Depletion of Melanoma fn14 by Oligonucleotide-Mediated Exon Skipping" Journal of Investigative Dermatology (2015) vol. 135, Supplement 1, pp. S106-S113.

Dias, N. et al., "Antisense Oligonucleotides: Basic Concepts and Mechanisms" Molecular Cancer Therapeutics (2002) vol. 1, pp. 347-355.

Giallourakis, C. et al., "Genome-Wide Analysis of Immune System Genes by EST Profiling" Journal of Immunology (2013) vol. 190, No. 11, pp. 5578-5587.

Hohenauer, T. et al., "The Prdm Family: Expanding Roles in Stem Cells and Development" Development (2012) vol. 139, pp. 2267-2282.

Leroy, G. et al., "A Quantitative Atlas of Histone Modification Signatures from Human Cancer Cells" Epigenetics & Chromatin (2013) vol. 6, No. 20, pp. 1-14.

Nishikawa, N. et al., "Gene Amplification and Overexpression of PRDM14 in Breast Cancer". Cancer Research (2007) vol. 67, No. 20, pp. 9649-9657.

Communication (Extended European Search Report) issued by the European Patent Office in European Application No. 17847101.7 dated Apr. 28, 2020, 8 pages total.

* cited by examiner

Primary Examiner — Ekaterina Poliakova-Georgantas
(74) Attorney, Agent, or Firm — Troutman Pepper Hamilton Sanders LLP

(57) ABSTRACT

The present invention relates to antisense oligonucleotides for modulating the activity of PRDM15 and use thereof in the treatment of cancer. In particular, said antisense oligonucleotides are capable of inducing the skipping of an exon of a PRDM15 mRNA. The present invention also relates to a method for determining prognosis in a patient with cancer, or selecting a therapeutic strategy for a patient with cancer, by assessing the level of PRDM15 nucleic acid, protein or activity in a sample.

Figure 1:
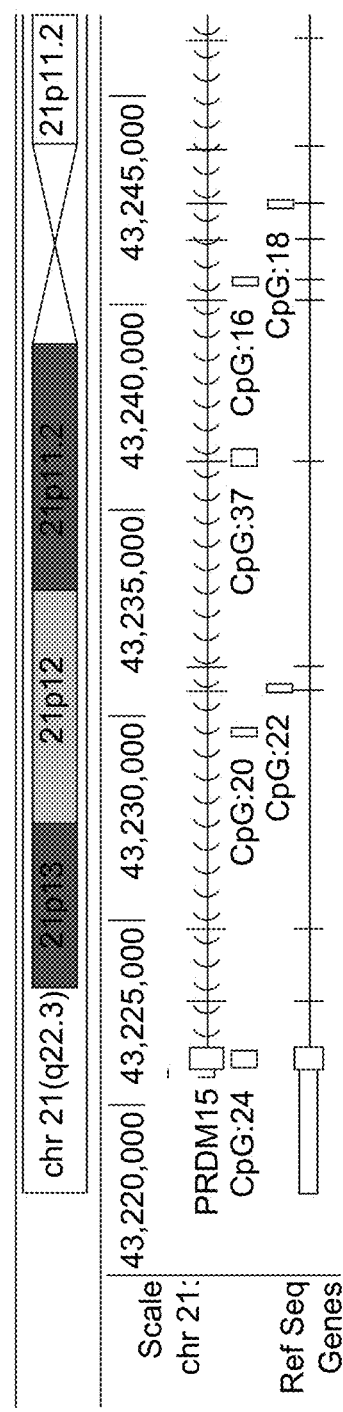
Figure 1:
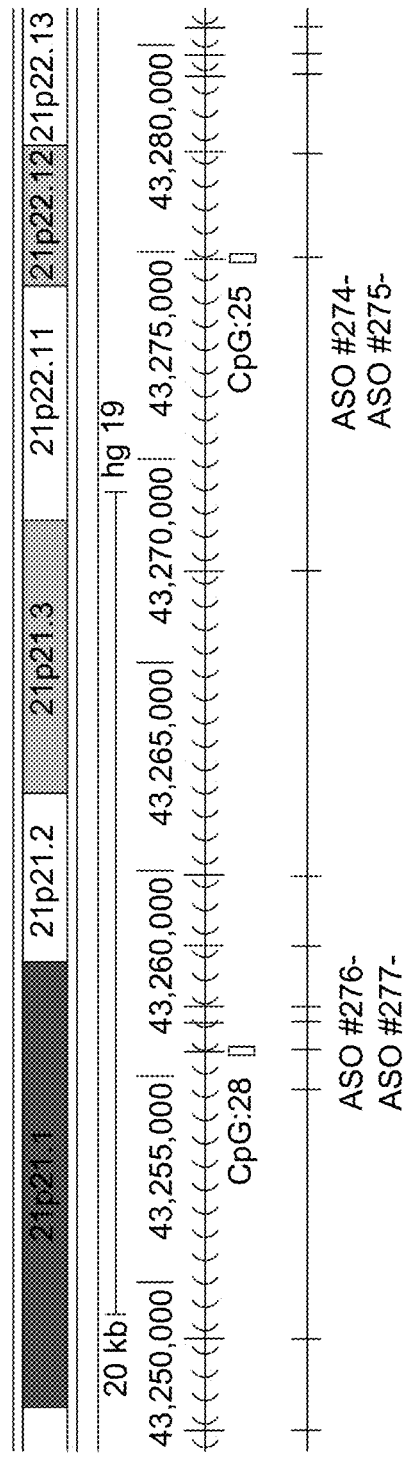
Figure 1:
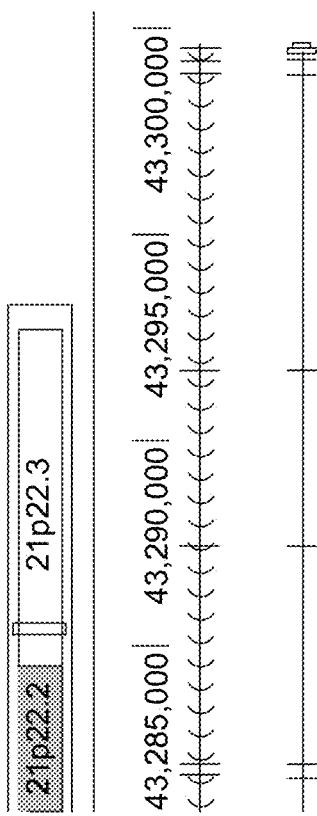

12 Claims, 14 Drawing Sheets
Specification includes a Sequence Listing.

METHOD OF TREATING CANCER BY ANTISENSE OLIGONUCLEOTIDES TARGETING PRDM15

CROSS-REFERENCE TO RELATED APPLICATIONS

This application is a U.S. National Phase application under 35 U.S.C. § 371 of International Patent Application No. PCT/SG2017/050436, filed on Sep. 4, 2017, which claims priority to Singapore Patent Application No. SG 10201607303Y, filed on Sep. 1, 2016, all of which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 25, 2019, is named 245866_000002_SL.txt and is 43,501 bytes in size.

The present invention relates to antisense oligonucleotides. In particular, the present invention relates to antisense oligonucleotides capable of inducing exon skipping of RNA.

More particular, the present application relates to the field of cancer, particularly to that of cancers overexpressing PR-domain containing protein 15 (PRDM15), such as lymphomas [follicular lymphoma, burkitt lymphoma, Diffuse Large B cell lymphoma], glioblastoma, breast-, prostate-, lung- and colon-cancer, etc. It is shown herein that direct and selective targeting of PRMD15 protein abundance [e.g. by Antisense OligoNucleotide (ASO)-mediated exon skipping], leads to cell cycle arrest and apoptosis of cancer cells. Also provided is evidence that complete deletion [e.g. by genetic deletion] or partial depletion [e.g. by Antisense OligoNucleotide (ASO)-mediated exon skipping] of PRDM15 in normal tissue has no adverse effects.

The PRDM family of proteins comprises of 16 and 17 members in mice and humans, respectively. All PRDMs share a common domain-structure, with a PR domain at the N-terminus, followed by a number of C2H2 zinc fingers at the C-terminus[1]. The latters are potentially involved in sequence-specific DNA-binding, and are essential for nuclear localisation[2,3]. The PR domain is functionally and structurally related to the SET [Su(var)[3-9], Enhancer-of-zeste [E(z)] and Trithorax (Trx)] domain, which is the catalytic domain of protein lysine methyltransferases (KMTs)[4]. Indeed, similar to SET domains, some, but not all, PR domains have been shown to possess intrinsic catalytic activity, directly methylating lysine residuess[5-11]. PRDM2 was the first member of the PRDM family to be validated as a tumour suppressor. Initially identified as an RB-interacting protein, the genomic locus containing PRDM2 (Chr.1p36) was then reported to be frequently deleted/rearranged in multiple cancer types[12-14]. Other PRDM genes display a similar pattern (e.g. PRDM1 (6q21-q22.1) and PRDM4 (12q23-q24.1)[15]). PRDM1 is indeed an established tumour suppressor in DLBCL and other haematological tumours[16]. Its expression is often silenced in ABC (Activated-B cell like)-DLBCL by multiple genetic and epigenetic mechanisms[17-19]. Mechanistically, PRDM1 depletion prevents B cell terminal differentiation and increases their proliferative capacity[20]. Conversely, its overexpression induced a G1 cell cycle arrest in DLBCL cells. Rare allelic variants of PRDM9, another member of the family, which is normally expressed exclusively in germ cells, have been recently linked to B-cell precursor acute lymphoblastic leukemia (B-ALL)[21,22], while PRDM11 was shown to act as a tumour suppressor in the Eµ-Myc Bcell lymphoma mouse model system[23].

PRDM15 is a poorly characterized member of the family, which is expressed at high levels (compared to normal tissues) in follicular and DLBCL lymphomas[24]. Small molecule inhibitors that selectively and efficiently target any of the PRDM family members have so far not been identified/introduced into the clinic.

The listing or discussion of an apparently prior-published document in this specification should not necessarily be taken as an acknowledgement that the document is part of the state of the art or is common general knowledge.

Any document referred to herein is hereby incorporated by reference in its entirety.

The present application relates to the field of cancer, particularly to that of cancers over-expressing PR-domain containing protein 15 (PRDM15), such as lymphomas [follicular lymphoma, burkitt lymphoma, Diffuse Large B cell lymphoma], glioblastoma, breast-, prostate-, lung- and colon-cancer, etc. It is shown herein that direct and selective targeting of PRMD15 protein abundance [e.g. by Antisense OligoNucleotide (ASO)-mediated exon skipping], leads to cell cycle arrest and apoptosis of cancer cells. Also provided is evidence that complete deletion [e.g. by genetic deletion] or partial depletion [e.g. by Antisense OligoNucleotide (ASO)-mediated exon skipping] of PRDM15 in normal tissue has no adverse effects.

In a first aspect of the present invention, there is provided an isolated antisense oligonucleotide for modulating the activity of PRDM15.

Preferably, the term modulating refers to the activation, inhibition, delay, repression or interference of one or more of; the activity of PRDM15; the RNA splicing or posttranslational processing to PRDM15; the phosphorylation of PRDM15; the level of expression of PRDM15 including both mRNA and/or pre-mRNA expression and protein expression; or the sub-cellular localisation of PRDM15. Preferably, in the present invention, the oligonucleotide modulates one or more of activity; or level of pre-mRNA, matured mRNA and protein expression. In various embodiments, the oligonucleotide inhibits the expression of PRDM15 or modify its expression products. In particular embodiments, the oligonucleotide inhibits the expression of PRDM15 by inducing the skipping of an exon of a PRDM15 pre-mRNA or mature mRNA to induce cell cycle arrest or apoptosis. More particularly, the oligonucleotide inhibits the expression of PRDM15 in a cell that overexpresses PRDM15.

Preferably, the oligonucleotide specifically hybridises to a target region of a PRDM15 pre-mRNA or mature mRNA. As used herein, "hybridisation" means an interaction between two or three strands of nucleic acids by hydrogen bonds in accordance with the rules of Watson-Crick DNA complementarity, Hoogstein binding, or other sequence specific binding known in the art. Hybridisation can be performed under different stringency conditions known in the art.

Preferably, the target region is any exon, intron or exon-intron boundary selected from the group comprising: exon 8, exon 9, exon 11, exon 12, exon 15, exon 16, exon 17, exon 18, exon 21, exon 24, exon 25, exon 29, intron 7, intron 8, intron 11, intron 12, intron 14 and intron 15. These sequences are shown in Table 1.

TABLE 1

| Exon/intron | SEQ ID NO: | Sequence |
|---|---|---|
| exon 8 | 74 | gtgtcagagatggctgaagatgggagcgaagagatcatgttcatct |
| exon 9 | 75 | ggtgtgaagactgcagccagtaccacgactccgaatgtcccgagctgggcccagtggtcatggtcaaagactcctttgtgttaagcagggcaag |
| exon 11 | 76 | gtcatccttcctcccaacttggagatcagacgactggaagatggagccgaggggtgttcgccatcactcagctcgtcaagcggacacagttcggtccctttgagtccaggagggtcgccaaatgggaaaaggagtctgcatttcccctgaag |
| exon 12 | 77 | gtgttccagaaggacgggcaccccgtgtgcttcgacacctccaacgaggatgactgcaactggatgatgctggtgcggccagcggcggaggccgagcaccagaacctgacggcctaccagcacggcagcgacgtgtacttcaccacctccagagacatccccccgggtaccgagctgcgcgtgtggtatgcggccttctatgccaagaagatggacaagcccatgctgaagcaggccggctctggcgtccacg |
| exon 15 | 78 | agcaagtggcagagatcattaccgaggtccctccggatgagcctgtgagtgcaacgccagatgagcggatcatggagctggttctggggaagctggccaccaccaccactgacaccagctcggttccaaa |
| exon 16 | 79 | gttcacccatcatcagaataacaccatcacgctcaagaggagcttaattctctcaagcagacacggcatccggcgcaagctcatcaaacagctcgggagcacaagcgggtttaccagtgcaatatctgcagcaagatcttccagaacagcagcaacctgagcaggcacgtgcgctcgcatg |
| exon 17 | 80 | gtgacaagctgttttaagtgcgaagagtgtgcaaaattgttcagccgcaaagagagcctaaagcagcacgtttcctacaagcacagcaggaacgag |
| exon 18 | 81 | gtggacggcgagtacaggtaccgctgcggcacttgtgagaagaccttccgcatcgagagcgcgctggagttccacaactgcaggacag |
| exon 21 | 82 | gagtgcggcgagtgaagcgagaggacctggaggccggtggggagaacctggtccgttacaagaaggagccttccggggtgcccggtgtgtggcaag |
| exon 24 | 83 | ctcaccttcggccgggggaaggagtacctgaagcacatcatggaggtgcacaaggagaagggctatgctgcagcatctgcaaccggcgcttgcactgaaggccacctaccacgcccacatggtcatccaccgtgaaaaacctgccggaccccaacgtgcagaa |
| exon 25 | 84 | gtacatccaccctgcgagatctgcgggcggatcttcaacagcatcgggaacctggagcgccacaagctcatccacacag |
| exon 29 | 85 | tgggcaagcagtggacgtgctccgtgtgcgacaagaagtacgtgaccgagtacatgctgcagaaagcacgttcagctcacacacgacaaggtggaggcgcagagctgccagctgtgcgggaccaaggtgtccaccagggcctccatgagccgacacatgcggcgcaagcaccccgag |
| intron 7 | 86 | gtgcgcacagttggggattggggggggggcagaggaggaataatcatttggtggcacatactgtgtgtatctcactttatgctcctcccaaactgcatgaggtgggtgttttatttccatttttacagcccaggaatgtgaggccccagaatgaacaatgtctagatccaccctgtgaatatatgtgtgtggggggtgtcagtttatgctcatctaccactatgcaagtgtttctggaggtgaacctcaaggatggataggaatagaattattggatctgataacagcttatgtgggagcacgagagttcctccacaacgtcacgcattgatttagtccccagagaagcaagtgttttatggggcaccaggcataggttaggagtgaggggaaaaaaagtgacaaccggctttttaaaaatggtgatataggtgggcacgatggcttgtgccataatcccagcactttgggaggctgaggtaggaggattgcttgagcccagcaggtagaggctgcagtgagccttgatcacaccactgcactccagcctgggcgacagacaagaccctgtcaccaaaaaaggtgatatatttgttttaaaaatggaaattgatggctaatatgaaaagatgaaagtctgagttcatgaggccattcaaatccattgctttcattaaaaataacattatttgaggtgagaagatgtttcagggatcccagccccatcccacaataagaggagaccccactgtgtgctctcttagaacaccacgtaatgttcctgtactggctggaggaggcctttagtaggaattgtctttaaacattattttggtaagaggccaggcacggtggctcacacctgtaatcccagcactttcagaggccgaggcaggcggatcacaaggtcaagagatcgagaccagcctggccaacatggtgaaaccccgtctctgctaaaaatacaaaaattagctgggtgtggtggctcacacctgtagtcccagctactcaggaggctgaggcaggagaatcacttgaacctgggaggcagaggttgcagtgagccaagatcctgccactgtactctatctatcctgggcaacagaggagctcaatttcaaaaacaaaacaaaagtattttggtaagagcttgtcattaatgaggctctcttgtatcctgacag |
| intron 8 | 87 | gtaagtgacccagggacctgtcccaggtccgagaccagccctatgtcatagaacacagatgggcgtggcgcttgctgtctgggcaaagccacgtctacatttggtttttataatatagaaaagctatatatttaaaatttccctatgaaacatttatttaataagcagtacactacaggggtatggttttaatagatcacctttctcagaactcctgcccgagggcacttgcaggggggtagcacttgattcagaaaagtaatccagggctaggcaggagggatgaacctgctaacattggccattttcatttatgctcattcttgggagagggtcttggtcttcgtcaccatggaggtgaccgtgcttgatttgaggcgtgcggcgggagctagagcttccctggggcgtgtcctgcctttgcactcctcatgtgtgcacgagtgctgacagaggccttcgggacacaggcctctgccatcaatgcaccctccttgcttgtcttttgcagtgtcggcatgcatgtgtctcatgactctgggtcaccctcatggggccagggtccccatttcccaggttttgtgttcttaggtgtctccctccctgggtgctcaatgcccggatgtctgcttgcag |
| intron 11 | 88 | gtaaaggctgttgccaaacaggagctcaggaactgggtgttttttctggcgttcccatgtgggaatggggagcaaggaccactgagtttccatgatttataaatgcctcaaaaacagctccaaatattgtaggtctgcttaatttccaagaaaatgtttcttttttacattgcaagagcatcgatattaagttagtattttgtaattttcaattttgcagaacactaaagagtgtgtttaagacatatgcaggagaaacccaa |

TABLE 1-continued

| Exon/intron | SEQ ID NO: | Sequence |
|---|---|---|
| | | atgctgactccagctgtcttacgacctccattgctgtcgcaggctttacgaggcagcgtcttgcag<br>gggcccatcgctctagttatttccacacctgtgcagagcgtatggtagtttgcaaacctctttcaa<br>agggaaggtgtttgtttaggcagtgatgagacattgggcaatagtgtgaagtttggccgttctaa<br>aaagcacatcagactgagagaagacagtggttctctactttgacgtgaactcgagaaaactaa<br>gatgtatgtaaattgcaaggcaggctttagaataagtaaaaaatgagccctctggaaggctatg<br>aggccaggcgaggctggttttgactgttgccatgcctgccctctgtatcgtaccccaagccagcc<br>agtcttcagaaatatctgtgaaataaacaaatgaggaatggggttgttagtcagcaaacttttctt<br>agagacccttgaaatggatctgcttgtcttaggacaggcagatgaagtcaacaagcttgggtttt<br>tggaagtcctttggaaagctgagcttgtaaggcagatttcagcaaaaagggggaagaaggaa<br>aggcacttgatttgtttacaaaagaaagaaggaaggaagggagggagggaaggagggaag<br>gaaggaagggagggagggagggaaggaaggaagggaaggaaggagggagggagggga<br>aggaaggaaaggaagggagggagggagggaggggaaggaagggagggagggaggggagg<br>gaaggaaggaaaggaagggagggagggagggagggaaggaaggaaaggaagggaggga<br>gggaggggagggaaggaaggagggagggagggaaggaaggaaggaaggaaggaaggaag<br>gagggagggagggagggaaggaaaggaaggaaggggagggagggagggagggaaggaa<br>aggaaggaaggagggagggagggagggaaggaaaggaaggaagggagggagggaggga<br>gggaaggaaaggaaggaaggaaggaaagaaaaggctgttttaagttgaagaaatatgtaaca<br>atgcttaaaacagcctcagaaagccgttggctacctgcctgtccttttgcagcacccatccggtc<br>gacgtacacagttggtgtgggtgcacggttgggggcgaggcccctttaaagaagtcttttgtgcc<br>cattttggtggtccttcagctacgcgattctgaaggtcatcgcctggtactgggttgttctcagtgc<br>atgcaccagcgttcagctcctctgtgcccaccagagagagcgtgccgccagctgggagcacac<br>ttcctcagcagctggtggtcattaggtgcctggtggtccccacccctgcctctcacttccaaggg<br>ctccgtctttggagaggcctctctaggagaagcttaggagagggggagagctctcttcctgcaggg<br>aggaagagaccatgacatcagaaaataaggaacaaaaccctcctatagtcatgtggttgatttg<br>aacttcaaaatatgtaagtttttctccctgctgcctgcctgcatttaatccataaagcaatagtgct<br>gtttgatagatggggaggcagctcataaagcctgaggagcccacccctgtggcggagctgg<br>gagtagaactgtgtcccagttcccagtgggccatctgagagccttaggtgtccccgtgacacgt<br>ggactgggagtgaagctcaggtagctcaaagcccacctggaccaggactagaactttggtgtcc<br>ccatgccactagaacctgattagaacttgagttccgcacctgggccgtgagtaacactcaggta<br>tcccaatgacacatagaccgctggctgtgtctgctgcttccttttgcctgtgactaacctgacccgt<br>ccaaaccacatggtctacctgtgaccctcctcactattgtaaacacctcaacatcccgtacagga<br>gcccttatggcctctgacgtggcactgtctagatgggttcctcagcacctgccccccacacgctga<br>tacacagatgggtaatcagccattcccggcttctccatgggccgactcaccttcag |
| intron 12 | 89 | gtatgtggcggccccgatccggagcccaccttcccttgtgcctcgccgaaggggttatggtcccttggctc<br>tgtgctgaccccacactgatgagatgggttgggctgggccagctgctgggatgcggagagtggaggagt<br>ggagagtcgggtctgtctttctgcttgttttaaacatccttggtcagtttgggcacgtggatgtaacacaagt<br>taacacagtgaggcagtgtttaacaacagagatacattctcagaaatgtgtcctggggcgatggcattgt<br>catgagtgcatggtagagcgcactctcgcgcaccttgatggcctggcctgctacacacccaggctgtatgg<br>tgtagcctgttctagctaccagcctgtccagcatgtgactgctactgcatgctgtgggcaactgtaacacatg<br>gtcagtatttgtctatgtaaacatagacaaagtaatagaggaaaaatactgtattagaatctcatgggacc<br>actgtctttgactgaaaccttgtcacatggcgcatgactgcttagctctgccctgggggctacgtgcagtga<br>gtgaccatcctcctaatcctatgaggctggggtactagccctgtcttttggacggaggaaacagcacaga<br>gaggttaaggaactgaccccaggtcacagtggagtagatgaagaaatcaggattggtccatgcacccg<br>gctccagtgttgctgctcaccgtgcaatggcctcctcccagatttgggggcagtgtgtgtgtgcgcgcgtgt<br>gcatacctgtgtgtgtgtgcatgcgtgttcaaagaaagccctagtgaaggttatgtgcgtgatctgcccaa<br>atctagcattcctgctgaaaaagccagtgcacagtgcctgtcctgtcctgctaagccggggtcagggcatcactttg<br>cccatcaagcgggggctgctgaattttaaatctttctcatccatgttatgggtctttttgacatagatcctcctc<br>ataaaacctgaagaaactctatgaaattcctggtatttgatgtcttttgacctgcaaaacagcaatttcata<br>ttgccgaagctgacactacccaggggagcaaatgttatttaatgttgccatgaagattctttgctcaaggg<br>ggcgaaatagatattgactctcctgacccccctcccaaatgacctgattctcatacgagcattgtttccttgt<br>tttataaatgcagtgtaatccaaaatattagtagctcggtagcttaagattcttaacttattggaaggttctg<br>gtctgtcctgtttgtcagtatgattgaggctttgtaaaatgcccctggttgtccctaatcccaggtccacaat<br>gggctgtgtgggagtgtcccggcgctgcgctgccccccataaaacaccagcaacccagtgccttcacgtca<br>gaaatgtgcctcccgcagtgctggaggccacacgcccacggtcagggtgtcagcagggctggtcccttct<br>gggcacccgtgagggagaatctgtcccgggactctcccaacctctggtggtggctggcacagtagcctttt<br>gtgtccccttggcttatggctgtgttactccagtctctgcctgtcttctctcccatgtctctgtgtcatctcttcat<br>aagaccaccgtcattggattcaggcctcccaatccagcatgacctcaccttaacttgatgacatctgca<br>cacatcctctcccaaaggtggtaggtggatgtgaattttggggagccactattgaacccactatgggccat<br>gtgagggctgggtggagagggccgctgggatgctgctggggagggttggtgaggagccaggcggct<br>ccctctggggcctgcagcggtggcggcgtcctcttcggccaggttggtaaagtgagctgagtgtactgggg<br>gcttcgcacccttcgcagagaaagactgtggctttgtggggagatgtttaagaatgaaaaggacaaaaa<br>gaacttggagaaacccactgctcttcacccagctgctcctagcccaccctcgtggctttgccaaaaccag<br>gtgcctgcctggcccagcacaagggagggcccctgtggtggtgcctgctgggtcagggggccgtttccaag<br>tcctgcgaggctgggctctctgagcagagccccaagtaactgtgatcttcgggacctgggctccttgtctctg<br>gaattcctgaaggcctaggcagctggcagcacgtgtgcccacgccagcccagactgcagccacgccgg<br>ggtttgggttctgagatgccggccttggccgtttacccccttgtcagcttgtatcctggggggatgccctcacc<br>acccctcaaggctaaggtcaaagcaaaggttgccacgccttattgcaaggtgtacaaggtgttcgtattcattttta<br>cctgctggagacccttcaatctggagctgagttttgaaacaatagatttaaatgaagtcagcctgggactgt<br>ggtgctcgaacagagtcgcctctgatttcggagatcctagggtaattcccattcctccctaaaacctctcaga<br>ataaaaggacacttgtaataattctaccaggacagtctgtgtaaatgggaacgtatggtcacctgagcat<br>agctaaacctaaacaaggtttttaattggggaaataaataaacaacttagttactcttagattttcagaaa<br>tgcttttttaggatggtcacttgttgtttgggggacaaatggcaagcagttatttctggagaggtagtgaacatg<br>gcgattccactcactggctggttgggtccttccttcccttcctttccccgagagagcccctgttgagctctgg<br>cttggcccttgaagtgctgccggctgccctggggaactttccctgggtccacctgctgattgttcaaatgg<br>caagccagcagccgcgtcaacacctgctcctcacacacacgctgcctgtcacccctctgcagccgctcag<br>cgccccgccacacacacactgcctctcaccctctgccacctatctggctccttcccctgagccctcctcc |

TABLE 1-continued

| Exon/intron | SEQ ID NO: | Sequence |
|---|---|---|
| | | ctgaccctgccagggggtccctctcgaggcacagtggcgcttctagagccctgcccgcccaatgcacccag<br>ggcccaccagagtctgagtgtgtgtcgagcacctccaccagctgaagctatgcactggagcccaacgctg<br>cctgcgtctcagaaatgagtatctcgatagataacaagaccttcgaagagaggctagaaacatccagaa<br>agctggccgcttgcccagttctcactgttcagactggatacgtgaaggactggagttctagggtaactgcg<br>taatcccactcctgctcagtgacgtgccctctggggtggacactcccagagagaacgctgctgcatggtgg<br>gagaaaaggaggccttttgtgcattgttgtacctctggcccagtgggagtaggcagagtgatgtgagtgg<br>cctccggggcattggtgtgctcctagaaccgtattggcagccgacgaacccaggaaccgtcttcctgtaa<br>attacttattgtggtggccgagtctttcctggtgagcgtgagagatcctaagactcagtgacttaattctgtc<br>tctttgatttgctccaaacatgcatcttcgtgtagaaatcagtcagttttgcagatcagtggcgccgtcttct<br>aaatacagagaaaactttggttttgtactgaaggagcagtaacacatcccttttaaaagtaacttattattt<br>tttctggtagtggattttacttttctagttccatctttttcttttttttgtagttttttgagatagggtctggcactg<br>ttgcccaggctggagtgcagtggcatgatcgtggctcactgcagccgccctcgtgggctcaagtgatcctc<br>ccacctcagcctccctagtagctgggaccacaggatgtgccaccacacccagctaatttttttaattttta<br>tttttagtagagatgggtctcactgtgttgcctaggctggtcttgaactcatggattcgggcaatcctcccac<br>cttccgaagtgctgggattccaggcgtgaagcactgtgcctggccttaacttgttcttgagctcacattaag<br>attgatttttgtttcttacaagaacctgaacctgctgacagatggaggggggcagccgaagaaacatcctgg<br>atcttcatgggagagagcatgaggcccaggaggagagtgttggggggggcaccaggaggaaagtgtggg<br>ggggcaccatgccagcagggcgttatgggacatccccgtccccaccagcttctgttccctttttagtctcg<br>ctctgagaatccgctgcttgaagaatcccacaagatcgtggacgaatggaaatcagagccagagtcccat<br>ttctcactcaccttctcaaacacacatgggttccaacgagaaaattttcaaaatcacctttctggtgaaaag<br>agtaaaatacaaacacattttataacattggggaaactgttcagtcacatatagcatcactgttctaactc<br>aactgctgttgccatttgattcgcattttctagtattttttaattttcattttattttttttgagacagagtct<br>tgctgtgtcacccaggctggaatgtggtggcccaatctcagctcactgcaacctctacctcccggttcaagc<br>aattctcttgcctcagcctccccagtagctgggattacaggcatgtaccatcatgcccagctaatttttttat<br>ttttagtagagatggggtttttgccatgttggccaggctggtgttgaactcctgacttgaagtgattcacctgc<br>ctcaacctcccaaagtgctgggattacaggcatgagccacctcactggcccctgtatttttaaaaaccagca<br>ctgatgacatatagtttacattcagtaagactcaacaattttaagtgtacagttcagagactttttttttttttt<br>taagtcagtctgtcgcccaggctggagtgcagtggtgtgatcttggctcactgcaacctccacctcccgagt<br>tcgagcaattctcatgcctcagcctctcaagagctgtaattacaggcgcatgccaccacgcctggctaattt<br>gtgcattttttagtagagacggcgttttgctatgttgcccaggctggtcttgagctcctggcctcaggtaatc<br>cacccatctgggcctcccaaagcgctgggattacaggcatgagccacagtgttcccgccagtttagagactt<br>tgagtgtctacagttgtataagcaccaccacagctgagttacagacctcgacttcatcccaggaagttctct<br>cgtgcggccctgcagtcagccgcgcccactggaatgccaggctgtttgctgtgctgtagctttgctgttcctt<br>ttttgtttgtttgttttaaactctgcatttttgcatagcggagctctagctgcacctcccatcttactgcttactt<br>ttctttgtgtgcacagtctggctcaccacatcttaggccttttttcctactgttactatctctggcatcactttaa<br>agctgtatgatgttagattttgctgggacacttctcttttgttggataatttaagtgattggcagtcaagaattg<br>ccttctgactgttaactaatattttcttcttaagaattcttatctttacaattactattcggaaaaccctgagt<br>gcttctcttgatgagcgggcagtcgtcatgacaagttttttctagtcctcttttacctagcagcagagcgccaa<br>gttgaggagaaccacacttgtgggggtggaggcttattgctggagacaatggcccacgtggattcga<br>agaaatttccccttattcagaagtggtggcttccagctaacctgggcccttgtcctcttttttctgaaactcaca<br>tgcgagtgttttttctctcttttggaacccgtgtatgtttgggaaggtgagtgggaaatgggaatttggctctga<br>tttccatttgtccttgatcttttgggattcttcaagcagcggattctcagagagcaagcgtaaaagggaaca<br>gaagctgtggggatggggtgtcccagaaaaatgccctgctgcagggtgccccccacacgttttctgc<br>tctttctttattttttagtatgacaaaaaatttcatattgcatttatgcctctttcttcttgttatcttatgaaaac<br>tcagaacatgcatgcacagggtgatagcagtaacctatatcttttttccttcattcattgcatccttagtgctg<br>gttttggatatgaaaagatacatgttttttttctagtgctgaatgcatatgcagttgtacttctggattattttttt<br>taaagacccaggagtttgtctttgtgggtggccctcggagtttgccgtgggtgatgaacttcaatgcaggct<br>gtatcgtgattagagtcgaagtgatgggcaggggtcctgccctgggcagccccagagctgccagacg<br>aggtgtagagaaactggcctgggccagatcatggtacactcacttaaaacgcctcccaattgtaggttgc<br>acaagagcatcagtgacttttttgttaaaaggtgcctgtagttctctttatagccaggcttacaccgcatgc<br>catgtaccccccagcttagctctccctcccccagattcctgctgtggcatggactgagggatagaggtgcttcct<br>gggatagcggccccctacctcaggtgcctatttaaaattaagttcaaacttagtaaaattaaacacttattt<br>cctggaacatgagccacatctggttagtggctgccttgctggataccagctgtggagcacgtcagtcatcc<br>acagaaagctctgccggatagcgctgggcgggagcagcagcccagccacacacgggggcgccactggc<br>tggccgtttgggggttccactgtctcttattctctatgagccagtgagagatgaggaattacacttggttcttgag<br>gaatgcacttttctcatgaagtcatataagggatgagtgccctctggactggcttcttggaggagttc<br>tcagctctgtgactggtgaccctgcagcaggcgtgtctctgtgctcagttgcctcatctgtgaaaagggggac<br>agtcacacgaccgtatcagccatgtgtgtaaagctctgaaaatggtgtctgtcatgtggagtgaccacag<br>gcccgtctgctgccgtcatcactgtcatcaccgcctctcagcacacacccctcctccgctgcgccgggattc<br>atggagacatatgagctgcttgggggtcaccttttttctcctctcatgtcttttgaag |
| intron 14 | 90 | gtgatgagcgggtcccggggatgagtgcctgcgtggggcgcagccctcctggcgcccgagggct<br>ggcggggcaggggggcagagggcggggcgggaaaactcagtgtagaaaggcctcgtggaagg<br>tagactctaagcccgtctgttttttctctcaatcaactctagtaaagtacaaatttccatgtaatacat<br>gtcacactaaaaaggatacagggtgtgaattttgacaaatggatacagctgtgaaaccagcac<br>ccccgtcagggtagaggacatttctgtctcgttagccactttcctgactgtcttctgtacgagttca<br>ttccacccatcctggaatttctcacgaatggactctgtctgcctccttcaggcagcttacagcctcg<br>agacccgcccacgtggtttatctgtggctccttctcctggattgctgaacagtgcttggtccatcac<br>ctgtgggtgggcactgagttgctcccaggacctgtctagggctcatcctttgattgtgcagtatcct<br>cagtgggtttgaagaggcatttgaccctcttccagggtgtgtggtctctgtaaggctcttgtccct<br>gtggtcctcacacagccccatccaagccacctgcagcacacgcctcgtgggcctcacagtgag<br>gatgagatctgatgctcagccactggccccttcacattttgttactgacactgggcagttttttctttt<br>actgtctgggatacaccaggatttctttttatgagagtgaaaaggagtccttattgcttctattaatt<br>agagacaattgggaagagcagccattgtggaatattctgagcctccccttttctgctgtgggtctg<br>cagcttctaggctgtgcactgttgggcgctgattttaggagcgcctgaaagcccctggccagtttc<br>cccaggtctctgtgaataggcagagaagatgggggcgggggaaagcgtgtcaggtagatattt<br>cactaattcttacttgtgttgagaagacatttagtaggcaaagtggtagaaaccagtggttgaat |

TABLE 1-continued

| Exon/intron | SEQ ID NO: | Sequence |
|---|---|---|
| | | tttttttgtgtaatcttcccctatttcatttatcttgggtttctggccagggtctccagtattggcgatg<br>atgtgatctttaactcttatacaaaatggttagctaaaatggttttttactaatgttggcacatttaat<br>tagaaacattaacatttctaaaactctgtcagaattgatgtagtaagttcgaagtttctgctatat<br>atccaaaatgttttggttggtatgaagagggattgaagtaatgttatgatgttgtggttttttaaa<br>agaataacaaattataacttcagtttaggctaagaaaaacattttgcttttctgtttgtactagtaa<br>atgtgtggatcccaaaatattgacagtttttttttttccctctgtaaacctcaacatttgtgcctacc<br>attctggcctggctgtggttcccatggggcagtgtgtcaccatggtttgactgtgtttgtcccctgc<br>tcttgtggttacttagcttgtcacatccccttcgtacag |
| intron 15 | 91 | gtaagtcctgcctggcacctggggccgtcctgtggacagacaatgctggcagcagccaggccat<br>tctggagggaaggcaccttcccagcaggaaagccccagggaaggagatggaaacagacctgc<br>tgaggaggcagcaggaatgttctggagctcaggaatgttctggagctcaggagtttaatggtgc<br>atccactgtgaaaacagctttagaaaaatgctttatttttggttaaatatgcataaatttaaccattt<br>taaccatgtttaagtgcacaatttagtggcattcaggatgttcacactgttgggcaatcatctccc<br>ccatccatctgtggaactttcccgtcttcccaagctgaaacgctgtccgcactaagcacccgctcc<br>agcccctccccagcccctggcacccaccattctactttctgtctctgtggatttgatgactctag<br>agatgtcttataagtggaatcagacaggatttgtccttatgtgactggcttattctaccccggctc<br>atccatgtgtagcctgtgtcagaattccttcaacactgagtaatataccatcatgcatatgcccc<br>atattttgtgtttccatgcatccattgatggacagttgggttgcttctagctttcgtgacgctgctgt<br>ggtaaaatactttgctatttgaatttcagtaaatataacagcttgccctgtgttttagttacgattct<br>tgggtcattttttaccatggagttgagtaagttggtggtcacttcttttttggccttttcggatcacct<br>cttatagttggcaaaagtaatatcagaaatgatgttacctgttttatttatttatactttatctttattg<br>cccagaagagttcaggtggcttaccatcaaaaatacatttaacagggaaaagaagttttgaaaa<br>tcaggttcagataatatgtaaaacagagaagagttaagacagagtgacaggagcagaaaaca<br>ggtgtggttattctaattgaggcacaaattgacctccaggctttctggtggccagagttagaaca<br>gagtcaggtgtgtggctgttgcagctaaagctgcctaatgtcattatatattcaaggtgtcccttttc<br>agatgccctggaagctgggagtgacgcccgggcgcattccctccttttctcgcatacaggtcggg<br>attagctgggaagttttggaaggaggccgttttcatgctgcttgtaacctggaactttttttcccacc<br>tgtcttttcccaacttattgacgtccctgggcag |

Preferably, the antisense oligonucleotide comprises a sequence selected from any one of SEQ ID NOs: 1 to 73. These sequences are shown in Table 2.

TABLE 2

| Sequence | SEQ. ID NO. | Target Exon |
|---|---|---|
| 5'-AUG AUC UCU UCG CUC CCA UCU UCA GCC AUC UC-3' | 1 | 8 |
| 5'-AAC AUG AUC UCU UCG CUC CCA UCU UCA-3' | 2 | 8 |
| 5'-AUU CGG AGU CGU GGU ACU GGC UGC AGU CUU CAC AC-3' | 3 | 9 |
| 5'-UCG GGA CAU UCG GAG UCG UGG UAC UGG CUG-3' | 4 | 9 |
| 5'-GGC CCA GCU CGG GAC AUU CGG AGU CGU GGU A-3' | 5 | 9 |
| 5'-CCA CUG GGC CCA GCU CGG GAC AUU CGG-3' | 6 | 9 |
| 5'-CUU UGA CCA UGA CCA CUG GGC CCA GCU CGG GAC AUU-3' | 7 | 9 |
| 5'-AUC UUC CAG UCG UCU GAU CUC CAA GUU GGG AGG AAG G-3' | 8 | 11 |
| 5'-AUU UGG CGA CCC UCC UGG ACU CAA AGG GAC CGA ACU GU-3' | 9 | 11 |
| 5'-CUC CUG GAC UCA AAG GGA CCG AAC UGU GUC CGC UUG A-3' | 10 | 11 |
| 5'-AAA GGG ACC GAA CUG UGU CCG CUU GAC GAG CUG A-3' | 11 | 11 |
| 5'-UCC UUU UCC CAU UUG GCG ACC CUC CUG GAC UCA AA-3' | 12 | 11 |
| 5'-GUU GGA GGU GUC GAA GCA CAC GGG GUG CCC GUC CUU-3' | 13 | 12 |
| 5'-CAU CAU CCA GUU GCA GUC AUC CUC GUU GGA GGU GU-3' | 14 | 12 |
| 5'-AGU CAU CCU CGU UGG AGG UGU CGA AGC AC-3' | 15 | 12 |
| 5'-GUG CUC GGC CUC CGC CGC UGG CCG CAC CAG CAU CA-3' | 16 | 12 |
| 5'-GUU CUG GUG CUC GGC CUC CGC CGC U-3' | 17 | 12 |

TABLE 2-continued

| Sequence | SEQ. ID NO. | Target Exon |
|---|---|---|
| 5'-UUG GAG GUG UCG AAG CAC ACG GGG UG-3' (ASO #274) | 18 | 12 |
| 5'-UCA UCC AGU UGC AGU CAU CCU CGU U-3' (ASO #275) | 19 | 12 |
| 5'-GUU GCA CUC ACA GGC UCA UCC GGA GGG ACC UCG GUA AUG AU-3' | 20 | 15 |
| 5'-UCC GGA GGG ACC UCG GUA AUG AUC UCU GCC ACU UGC U-3' | 21 | 15 |
| 5'-UCA UCU GGC GUU GCA CUC ACA GGC UCA UCC GGA GGG A-3' | 22 | 15 |
| 5'-CAU GAU CCG CUC AUC UGG CGU UGC ACU CAC AGG CU-3' | 23 | 15 |
| 5'-UGG UGG UGG CCA GCU UCC CCA GAA CCA GCU CCA UGA UC-3' | 24 | 15 |
| 5'-GCU UCC CCA GAA CCA GCU CCA UGA UCC GCU CAU C-3' | 25 | 15 |
| 5'-ACU CAC AGG CUC AUC CGG AGG GAC-3' (ASO #276) | 26 | 15 |
| 5'-GGA CCU CGG UAA UGA UCU CUG CCA CUU GC-3' (ASO #277) | 27 | 15 |
| 5'-GUG AUG GUG UUA UUC UGA UGA UGG GUG AAC-3' | 28 | 16 |
| 5'-UUA AGC UCC UCU UGA GCG UGA UGG UGU UAU UCU GAU GA-3' | 29 | 16 |
| 5'-UUG CGC CGG AUG CCG UGU CUG CUU GAG AGA AUU AAG C-3' | 30 | 16 |
| 5'-UGU UUG AUG AGC UUG CGC CGG AUG CCG UGU CU-3' | 31 | 16 |
| 5'-UCU CUU UGC GGC UGA ACA AUU UGC ACA CUU CGC ACU U-3' | 32 | 17 |
| 5'-ACA AUU UGC ACA CUU CGC ACU UAA ACA GCU UGU CAC-3' | 33 | 17 |
| 5'-UUA GGC UCU CUU UGC GGC UGA ACA AUU UGC ACA CU-3' | 34 | 17 |
| 5'-CGU GCU GCU UUA GGC UCU CUU UGC GGC UGA ACA AUU UU-3' | 35 | 17 |
| 5'-CUU GUA GGA AAC GUG CUG CUU UAG GCU CUC UUU G-3' | 36 | 17 |
| 5'-CUC GUU CCU GCU GUG CUU GUA GGA AAC GUG CUG CUU UAG-3' | 37 | 17 |
| 5'-AAG UGC CGC AGC GGU ACC UGU ACU CGC CGU C-3' | 38 | 18 |
| 5'-GAA GGU CUU CUC ACA AGU GCC GCA GCG UAC CUG UAC UCG G-3' | 39 | 18 |
| 5'-UCG AUG CGG AAG GUC UUC UCA CAA GUG CCG CAG-3' | 40 | 18 |
| 5'-UGG AAC UCC AGC GCG CUC UCG AUG CGG AAG GUC UUC U-3' | 41 | 18 |
| 5'-AGU UGU GGA ACU CCA GCG CGC UCU CGA UGC GGA AGG UC-3' | 42 | 18 |
| 5'-UGU CCU GCA GUU GUG GAA CUC CAG CGC GCU CUC GAU-3' | 43 | 18 |
| 5'-CCA CCG GCC UCC AGG UCC UCU CGC UUC ACU CGC CGC-3' | 44 | 21 |
| 5'-GGU UCU CCC CAC CGG CCU CCA GGU CCU CUC GCU UCA CU-3' | 45 | 21 |
| 5'-CUU CUU GUA ACG GAC CAG GUU CUC CCC ACC GGC CUC-3' | 46 | 21 |
| 5'-UGU AAC GGA CCA GGU UCU CCC CAC CGG CCU CCA GGU-3' | 47 | 21 |
| 5'-AAG GCU CCU UCU GUA ACG GAC CAG GUU CUC CCC ACC CG-3' | 48 | 21 |
| 5'-GCA CCC GGA AGG CUC CUU CUU GUA ACG GAC CAG GUU-3' | 49 | 21 |
| 5'-ACA CAC CGG GCA CCC GGA AGG CUC CUU CUU GUA AC-3' | 50 | 21 |
| 5'-CUU GCC ACA CAC CGG GCA CCC GGA AGG CUC CUU CU-3' | 51 | 21 |
| 5'-ACC GGG CAC CCG GAA GGC UCC UUC UUG UAA CGG AC-3' | 52 | 21 |
| 5'-UUC AGG UAC UCC UUC CCC CGG CCG AAG GUG AG-3' | 53 | 24 |
| 5'-UCU CCU UGU GCA CCU CCA UGA UGU GCU UCA GGU ACU CCU-3' | 54 | 24 |
| 5'-CAU AGC CCU UCU CCU UGU GCA CCU CCA UGA UG-3' | 55 | 24 |

TABLE 2-continued

| Sequence | SEQ. ID NO. | Target Exon |
|---|---|---|
| 5'-AGU GCA AAG CGC CGG UUG CAG AUG CUG CAG CCA UA-3' | 56 | 24 |
| 5'-GUA GGU GGC CUU CAG UGC AAA GCG CCG GU-3' | 57 | 24 |
| 5'-GGA UGA CCA UGU GGG CGU GGU AGG UGG CCU UCA GUG C-3' | 58 | 24 |
| 5'-CCC GCA GAU CUC GCA GGG GUG GAU GU-3' | 59 | 25 |
| 5'-GGC GCU CCA GGU UCC CGA UGC UGU UGA AGA UCC GCC CG-3' | 60 | 25 |
| 5'-UGU GUG GAU GAG CUU GUG GCG CUC CAG GUU CCC GAU G-3' | 61 | 25 |
| 5'-UUC UUG UCG CAC ACG GAG CAC GUC CAC UGC UUG-3' | 62 | 29 |
| 5'-GGU CAC GUA CUU CUU GUC GCA CAC GGA GCA CGU CC-3' | 63 | 29 |
| 5'-CGU GCU UCU GCA GCA UGU ACU CGG UCA CGU ACU UCU UGU C-3' | 64 | 29 |
| 5'-CUG AAC GUG CUU CUG CAG CAU GUA CUC GGU CAC GU-3' | 65 | 29 |
| 5'-CUU GUC GUG UGU GAG CUG AAC GUG CUU CUG C-3' | 66 | 29 |
| 5'-CAC AGC UGG CAG CUC UGC GCC UCC ACC UUG UCG UGU GU-3' | 67 | 29 |
| 5'-UGG UGG ACA CCU UGG UCC CGC ACA GCU GGC AGC UCU-3' | 68 | 29 |
| 5'-UAA GCU CCU CUU GAG CGU GAU GGU GUU AU-3' | 69 | 16 |
| 5'-UUG CGG CUG AAC AAU UUU GCA CAC UCU U-3' | 70 | 17 |
| 5'-UUU AGG CUC UCU UUG CGG CUG AAC AAU UU-3' | 71 | 17 |
| 5'-CAC UCU UCG CAC UUA AAC AGC UUG UCA-3' | 72 | 17 |
| 5'-UUG UAG GAA ACG UGC UGC UUU AGG CUC UC-3' | 73 | 17 |

Table 2 not only shows the various sequences of the antisense oligonucleotides of the present invention, it also shows the sequences respective target exons that are shown in Table 1. In various embodiments of the present invention, each sequence set out in Table 2 may target one or more exons. For example SEQ ID NO. 69 targets exon 16, SEQ ID Nos. 70 to 73 target exon 17.

By "oligonucleotide", it is meant to refer to any polynucleotide. a "polynucleotide" is an oligomer comprised of nucleotides. A polynucleotide may be comprised of DNA, RNA modified forms thereof, or a combination thereof. The term "nucleotide" or its plural as used herein is interchangeable with modified forms as discussed herein and otherwise known in the art. In certain instances, the art uses the term "nucleobase" which embraces naturally occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C[3]-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et ah, U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et ah), in Chapter 15 by Sanghvi, in Antisense Research and Application, Ed. S. T. Crooke and B. Lebleu, CRC Press, 1993, in Englisch et ah, 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which is hereby incorporated by reference in its entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles {e.g., 5-nitroindole), and optionally substituted hypoxanthine. Other desirable universal bases include pyrrole, and diazole or triazole derivatives, including those universal bases known in the art.

Polynucleotides may also include modified nucleobases. A "modified base" is understood in the art to be one that can pair with a natural base {e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include, without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (IH-pyrimido[5,4-b][I,4]benzoxazin-2(3H)-one), phenothiazine cytidine (IH-pyrimido[5,4-b] [I,4]benzothiazin-2(3H)-one), G-clamps such as a substituted phenoxazine cytidine (e.g. 9-(2-aminoethoxy)-H-pyrimido[5,4-b] [I,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et ah, 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity of the polynucleotide and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.deg. C. and are, in certain aspects, combined with 2'-O-methoxyethyl sugar modifications. See, U. S. Pat. Nos. 3,687,808, 4,845,205; 5,130,302; 5,134,066; 5,175,273; 5,367,066; 5,432,272; 5,457,187; 5,459,255; 5,484,908; 5,502, 177; 5,525,711; 5,552,540; 5,587,469; 5,594, 121, 5,596,091; 5,614,617; 5,645,985; 5,830,653; 5,763,588; 6,005,096; 5,750,692 and 5,681,941, the disclosures of which are incorporated herein by reference.

Those of skill in the art can readily design antisense polynucleotides according to the present disclosure. For example, general teachings in the art include, but are not limited to, Aartsma-Rus et al, Methods Mol Biol. 867: 117-29 (2012); Aartsma-Rus et al, Methods Mol Biol. 867: 97-116 (2012); van Roon-Mom et al., Methods Mol Biol. 867: 79-96 (2012), each of which is incorporated herein by reference. General guidelines also include attempting to avoid 3 consecutive G or C nucleotides, choosing lengths and sequences that favour self structure (hairpinning will be avoided), and avoiding those sequences likely to form primer dimers. In some embodiments, an antisense polynucleotide of the disclosure is one that is designed to specifically hybridize to an exon or an intron or an intron-exon boundary, such that the antisense polynucleotide specifically hybridises to a sequence that is completely within an exon of a PRDM15 nucleic acid, or about one nucleotide of the antisense polynucleotide spans said intron-exon boundary when the antisense polynucleotide is specifically hybridised to the PRDM15 nucleic acid. In some embodiments wherein the antisense polynucleotide specifically hybridizes to a sequence that is completely within an exon, it is contemplated that a terminus of the antisense polynucleotide is about 1, 2, 3, 4, 5, 6, 7, 8, 9, 10 or more nucleotides from a terminus of the exon.

In further embodiments, an antisense polynucleotide of the disclosure is one that is designed to specifically hybridize to an intron-exon boundary of a PRDM15 nucleic acid, such that about 2, 3, 4, 5, 6, 7, 8, 9, 10 or more nucleotides of the antisense polynucleotide span said intron-exon boundary. It is understood that a nucleotide can "span the intron-exon boundary" on either the exon side or intron side. Thus, an antisense polynucleotide that specifically and predominantly hybridises to intronic sequence and only hybridizes to one nucleotide of an adjoining exon would "span the intron-exon boundary" by one nucleotide. Similarly, an antisense polynucleotide that specifically hybridizes to exonic sequence and only hybridises to one nucleotide of an adjoining intron would "span the intron-exon boundary" by one nucleotide. In any of the aforementioned embodiments, the antisense polynucleotide is at least about 10 nucleotides and up to about 15, 20, 25, 30, 35, 40, 45, 50 or more nucleotides in length.

Modified polynucleotides are contemplated for use wherein both one or more sugar and/or one or more internucleotide linkage of the nucleotide units in the polynucleotide is replaced with "non-naturally occurring" sugars (i.e., sugars other than ribose or deoxyribose) or internucleotide linkages, respectively. In one aspect, this embodiment contemplates a peptide nucleic acid (PNA). In PNA compounds, the sugar-backbone of a polynucleotide is replaced with an amide-containing (e.g., peptide bonds between N-(2-aminoethyl)-glycine units) backbone. See, for example U.S. Pat. Nos. 5,539,082; 5,714,331; and 5,719,262, and Nielsen et ah, Science, 1991, 254, 1497-1500, the disclosures of which are herein incorporated by reference. [0105] Modified polynucleotides may also contain one or more substituted sugar groups. In one aspect, a modification of the sugar includes Locked Nucleic Acids (LNAs) in which the 2'-hydroxyl group is linked to the 3' or 4' carbon atom of the sugar ring, thereby forming a bicyclic sugar group. The linkage is in certain aspects a methylene (—CH[2]-)[n] group bridging the 2' oxygen atom and the 4' carbon atom wherein n is 1 or 2. LNAs and preparation thereof are described in WO 98/39352 and WO 99/14226, the disclosures of which are incorporated herein by reference. In the present invention, preferably, the antisense oligonucleotide comprises a modified polynucleotide backbone. The modified polynucleotide backbone comprises a modified moiety substituted for the sugar of at least one of the polynucleotides. The modified moiety may be selected from the group comprising of phosphorodiamidate morpholino oligomer (PMO), peptide-conjugated phosphorodiamidate morpholino oligomer (PPMO), and non-peptide dendrimeric octaguanidine moiety-tagged morpholino oligomer.

In various embodiments, the modified polynucleotide backbone comprises at least one modified internucleotide linkage. The modified internucleotide linkage comprises a modified phosphate. More preferably, the modified phosphate is any one selected from the group comprising of a non-bridging oxygen atom substituting a sulfur atom, a phosphonate, a phosphorothioate, a phosphodiester, a phosphoromorpholidate, a phosphoropiperazidate and a phosphoroamidate.

In various embodiment of the invention, the antisense oligonucleotide comprises a backbone selected from the group comprising of ribonucleic acid, deoxyribonucleic acid, DNA phosphorothioate, RNA phosphorothioate, 2'-O- methyl-oligoribonucleotide and 2'-O-methyl-oligodeoxyribonucleotide, 2'-O-hydrocarbyl ribonucleic acid, 2'-O-hydrocarbyl DNA, 2'-O-hydrocarbyl RNA phosphorothioate, 2'-O-hydrocarbyl DNA phosphorothioate, 2'-F-phosphorothioate, 2'-F-phosphodiester, 2'-methoxyethyl phosphorothioate, 2-methoxyethyl phosphodiester, deoxy methylene(methylimino) (deoxy MMI), 2'-O-hydrocarby MMI, deoxymethylphos-phonate, 2'-O-hydrocarbyl methylphosphonate, morpholino, 4'-thio DNA, 4'-thio RNA, peptide nucleic acid, 3'-amidate, deoxy 3'-amidate, 2'-O-hydrocarbyl 3'-amidate, locked nucleic acid, cyclohexane nucleic acid, tricycle-DNA, 2'fluoro-arabino nucleic acid, N3'-P5' phosphoroamidate, carbamate linked, phosphotriester linked, a nylon backbone modification and mixtures of the aforementioned backbones.

Preferably, the oligonucleotide is chemically linked to one or more conjugates that enhance the activity, cellular distribution, or cellular uptake of the antisense oligonucleotide.

The compounds of the disclosure also can be used as a prophylactic or therapeutic, which may be utilized for the purpose of treatment of a genetic disease. In an embodiment, the antisense oligonucleotide may be used in treating a PRDM15-expressing cancer patient. The patient may be administered a further anti-cancer agent or treatment. The cancer is any one selected from the group comprising: haematological malignancies, lung cancer, breast cancer, prostate cancer, stomach cancer, testis cancer, larynx cancer, liver cancer, uterus cancer, colorectal cancer, melanoma, glioblastoma, sarcomas, and retinoblastoma. The haematological malignancies is either lymphoma or leukaemia. In particular, the lymphoma is a B-cell lymphoma. More particularly, the B-cell lymphoma is a follicular lymphoma or a diffuse large B-cell lymphoma.

In another aspect of the present invention, there is provided a pharmaceutical composition comprising the antisense oligonucleotide according to the first aspect of the invention and a pharmaceutically acceptable carrier. The composition is suitable for parenteral administration either naked or complexed with a delivery agent to a patient. The carrier is selected from the group consisting of a nanoparticle, such as a polymeric nanoparticle; a liposome, such as pH-sensitive liposome, an antibody conjugated liposome; a viral vector, a cationic lipid, a polymer, a UsnRNA, such as U7 snRNA and a cell penetrating peptide. The antisense oligonucleotide is administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular.

A pharmaceutically acceptable carrier refers, generally, to materials that are suitable for administration to a subject wherein the carrier is not biologically harmful, or otherwise, causes undesirable effects. Such carriers are typically inert ingredients of a medicament. Typically a carrier is administered to a subject along with an active ingredient without causing any undesirable biological effects or interacting in a deleterious manner with any of the other components of a pharmaceutical composition in which it is contained. Suitable pharmaceutical carriers are described in Martin, Remington's Pharmaceutical Sciences, 18th Ed., Mack Publishing Co., Easton, Pa., (1990), incorporated by reference herein in its entirety.

In a more specific form of the disclosure there are provided pharmaceutical compositions comprising therapeutically effective amounts of an antisense polynucleotide together with pharmaceutically acceptable diluents, preservatives, solubilizers, emulsifiers, adjuvants and/or carriers. Such compositions include diluents of various buffer content (e.g., phosphate, Tris-HCl, acetate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as, for example and without limitation, polylactic acid or polyglycolic acid, or into liposomes. Hylauronic acid may also be used. Such compositions may influence the physical state, stability, rate of in vivo release, and rate of in vivo clearance of the disclosed compositions. The compositions may be prepared in liquid form, or may be in dried powder, such as lyophilized form.

It will be appreciated that pharmaceutical compositions provided according to the disclosure may be administered by any means known in the art. Preferably, the pharmaceutical compositions for administration are administered by injection, orally, or by the pulmonary, or nasal route. The antisense polynucleotides are, in various embodiments, delivered by intravenous, intra-arterial, intraperitoneal, intramuscular, or subcutaneous routes of administration.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For polynucleotides, preferred examples of pharmaceutically acceptable salts include, but are not limited to, (a) salts formed with cations such as sodium, potassium, ammonium, magnesium, calcium, polyamines such as spermine and spermidine; (b) acid addition salts formed with inorganic acids, for example hydrochloric acid, hydrobromic acid, sulfuric acid, phosphoric acid, nitric acid; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid; and (d) salts formed from elemental anions such as chlorine, bromine, and iodine. The pharmaceutical compositions of the disclosure may be administered in a number of ways depending upon whether local or systemic treatment is desired and upon the area to be treated. Administration may be topical (including ophthalmic and to mucous membranes including rectal delivery), pulmonary, e.g., by inhalation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Polynucleotides with at least one 2'-O-methoxyethyl modification are believed to be particularly useful for oral administration.

The pharmaceutical formulations of the disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly bringing into association the active ingredients with liquid carriers or finely divided solid carriers or both, and then, if necessary, shaping the product.

Combination therapy with an additional therapeutic agent is also contemplated by the disclosure. Examples of therapeutic agents that may be delivered concomitantly with a composition of the disclosure include, without limitation, a glucocorticoid steroid (for example and without limitation, prednisone and deflazacort), an angiotensin converting enzyme inhibitor, a beta adrenergic receptor blocker, an anti-fibrotic agent and a combination thereof.

In some embodiments, the present invention may be used in gene therapy such, e.g. using a vector (e.g., an expression vector) comprising a polynucleotide of the invention to direct expression of the polynucleotide in a suitable host cell. Such vectors are useful, e.g., for amplifying the polynucleotides in host cells to create useful quantities thereof, and for expressing proteins using recombinant techniques. In some embodiments, the vector is an expression vector wherein a polynucleotide of the invention is operatively linked to a polynucleotide comprising an expression control sequence.

As such, yet another aspect of the present invention provides for a method of treating cancer in a patient, the method comprising administering an antisense oligonucleotide according to the first aspect of the invention, or a pharmaceutically effective amount of a composition comprising the antisense oligonucleotide. The carrier is selected from the group consisting of a nanoparticle, such as a polymeric nanoparticle; a liposome, such as pH-sensitive liposome, an antibody conjugated liposome; a viral vector, a cationic lipid, a polymer, a UsnRNA, such as U7 snRNA and a cell penetrating peptide.

The antisense oligonucleotide or composition may be administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular. Having said that, proven systemic administration options include intravenous, intraperitoneal, intranasal and intrathecal. Complexing of ASOs with delivery carriers such as nanoparticles, polymer- or liposome-based vehicles can further augment the delivery efficiency of ASOs to specific tissues.

The cancer is any one selected from the group comprising: haematological malignancies, lung cancer, breast cancer, prostate cancer, stomach cancer, testis cancer, larynx cancer, liver cancer, uterus cancer, colorectal cancer, melanoma, glioblastoma, sarcomas, and retinoblastoma.

In another aspect of the present invention, there is provided a method for aiding in categorising or determining prognosis in a patient with cancer, or in selecting a therapeutic strategy for a patient with cancer, the method comprising assessing the level of PRDM15 nucleic acid, protein or activity in a sample. The method comprises the step of selecting a treatment regime making use of the information on the level of PRDM15 nucleic acid, protein or activity in the sample. In various embodiments, the sample is obtained from the patient and the sample is a tissue sample in which cancer is suspected or in which cancer has been found, or contains cells from said tissue. If the level of PRDM15 nucleic acid, protein or activity in the sample is an elevated level, then the selected treatment regime comprises treating the patient with an inhibitor of PRDM15 activity or modulator of PRDM15's pre-mRNA, mRNA and protein expression levels. In various embodiments, the inhibitor or modulator comprises an antisense oligonucleotide according to the first aspect of the present invention.

In another aspect of the present invention, there is provided a method of inducing exon-skipping of a PRDM15 pre-mRNA, the method comprising delivering to a cell the antisense polynucleotide according to the first aspect of the present invention, or the pharmaceutical composition comprising the antisense oligonucleotide, thereby inducing exon-skipping of the PRDM15 pre-mRNA.

Preferably, exons 12 and/or exon 15 is/are skipped.

In various embodiments, the cell is a human cell. The human cell is a cancer cell, the cancer is any one selected from the group comprising: haematological malignancies, lung cancer, breast cancer, prostate cancer, stomach cancer, testis cancer, larynx cancer, liver cancer, uterus cancer, colorectal cancer, melanoma, glioblastoma, sarcomas, and retinoblastoma.

In another aspect of the present invention, there is provided a kit comprising the antisense oligonucleotide according to the first aspect of the present, optionally in a container, and a package insert, package label, instructions or other labelling.

Those of ordinary skill in the art will appreciate that applications of the above method has wide application for identifying antisense molecules suitable for use in the treatment of many other diseases.

Advantageously, the present invention provides for a novel target in oncology (PRDM15). There is no report that targeting PRDM15 could be beneficial as antitumor therapy. In particular, the present invention using antisense oligonucleotides to induce exon skipping in the expression of PRDM15. The use of ASO to induce PRDM15 Exon15 skipping and subsequent reduction of PRDM15 protein levels is novel. The invention may be used to develop novel chemical formulas for a group of highly efficacious (IC50<25 nM) drug candidates against PRDM15 for multiple cancers.

In order that the present invention may be fully understood and readily put into practical effect, there shall now be described by way of non-limitative examples only preferred embodiments of the present invention, the description being with reference to the accompanying illustrative figures.

In the Figures:

FIG. 1 Schematic representation of the human PRDM15 genomic locus. Location of each ASO is indicated. Sequences are as follow:

ASO #274:

(SEQ ID NO: 18)
UUG GAG GUG UCG AAG CAC ACG GGG UG (SEQ ID NO: 92)
[mU]*[mU]*[mG]*[mG]*[mA]*[mG]*[mG]*[mU]*[mG]*[mU]*

[mC]*[mG]*[mA]*[mA]*[mG]*[mC]*[mA]*[mC]*[mA]*[mC]*

[mG]*[mG]*[mG]*[mG]*[mU]*[mG]*

-continued

ASO #275:
(SEQ ID NO: 19)
UCA UCC AGU UGC AGU CAU CCU CGU U (SEQ ID NO: 93)
[mU]*[mC]*[mA]*[mU]*[mC]*[mC]*[mA]*[mG]*[mU]*[mU]*

[mG]*[mC]*[mA]*[mG]*[mU]*[mC]*[mA]*[mU]*[mC]*[mC]*

[mU]*[mC]*[mG]*[mU]*[mU]*

ASO #276:
(SEQ ID NO: 26)
ACU CAC AGG CUC AUC CGG AGG GAC (SEQ ID NO: 94)
[mA]*[mC]*[mU]*[mC]*[mA]*[mC]*[mA]*[mG]*[mG]*[mC]*

[mU]*[mC]*[mA]*[mU]*[mC]*[mC]*[mG]*[mG]*[mA]*[mG]*

[mG]*[mG]*[mA]*[mC]*

ASO #277:
(SEQ ID NO: 27)
GGA CCU CGG UAA UGA UCU CUG CCA CUU GC (SEQ ID NO: 95)
[mG]*[mG]*[mA]*[mC]*[mC]*[mU]*[mC]*[mG]*[mG]*[mU]*

[mA]*[mA]*[mU]*[mG]*[mA]*[mU]*[mC]*[mU]*[mC]*[mU]*

[mG]*[mC]*[mC]*[mA]*[mC]*[mU]*[mU]*[mG]*[mC]*
* = PHOSPHOROTHIOATE LINKAGE
[mA], [mU], [mG], [mc]= 2'O-METHYL RNA

Figure 2:
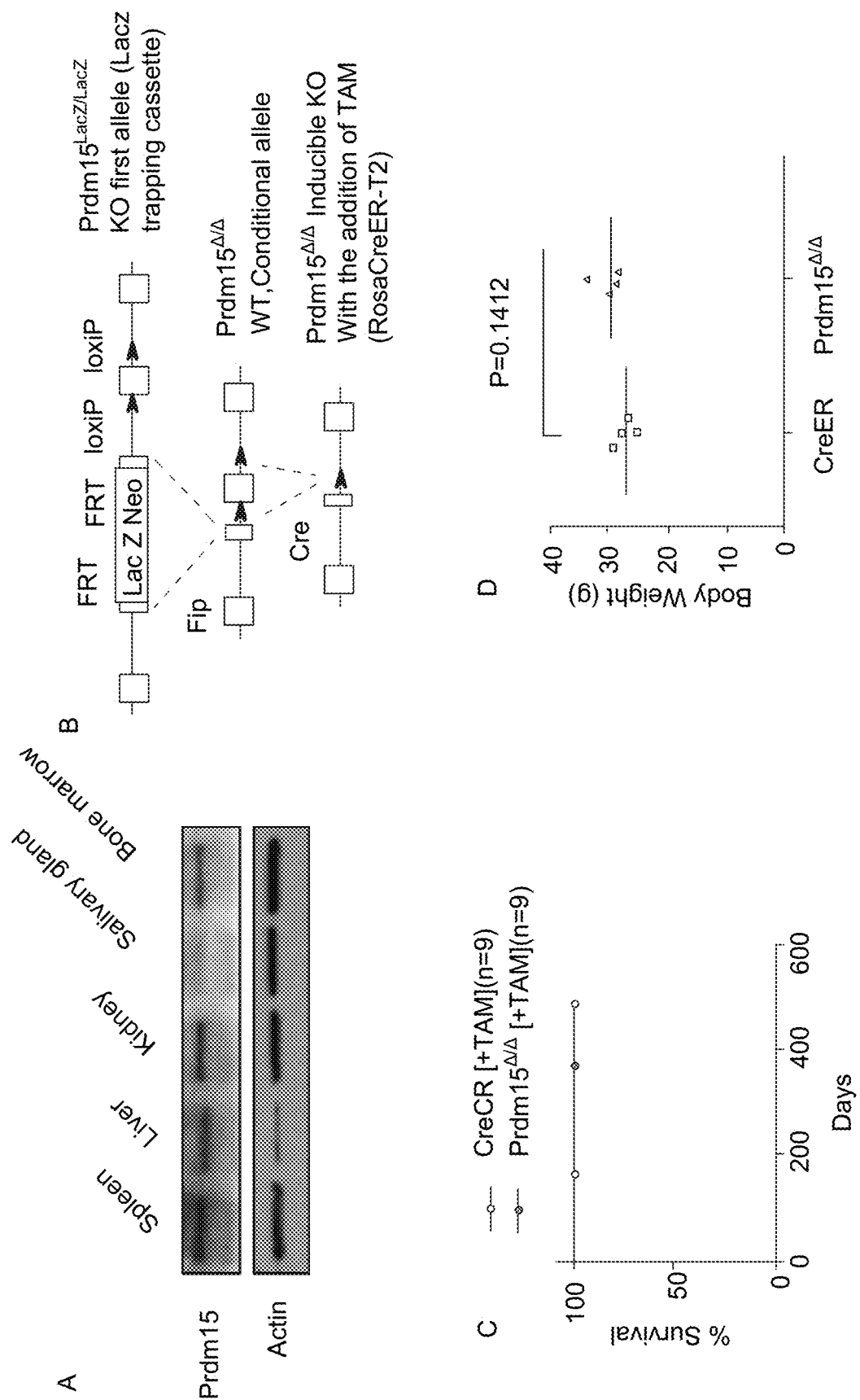
Figure 2:
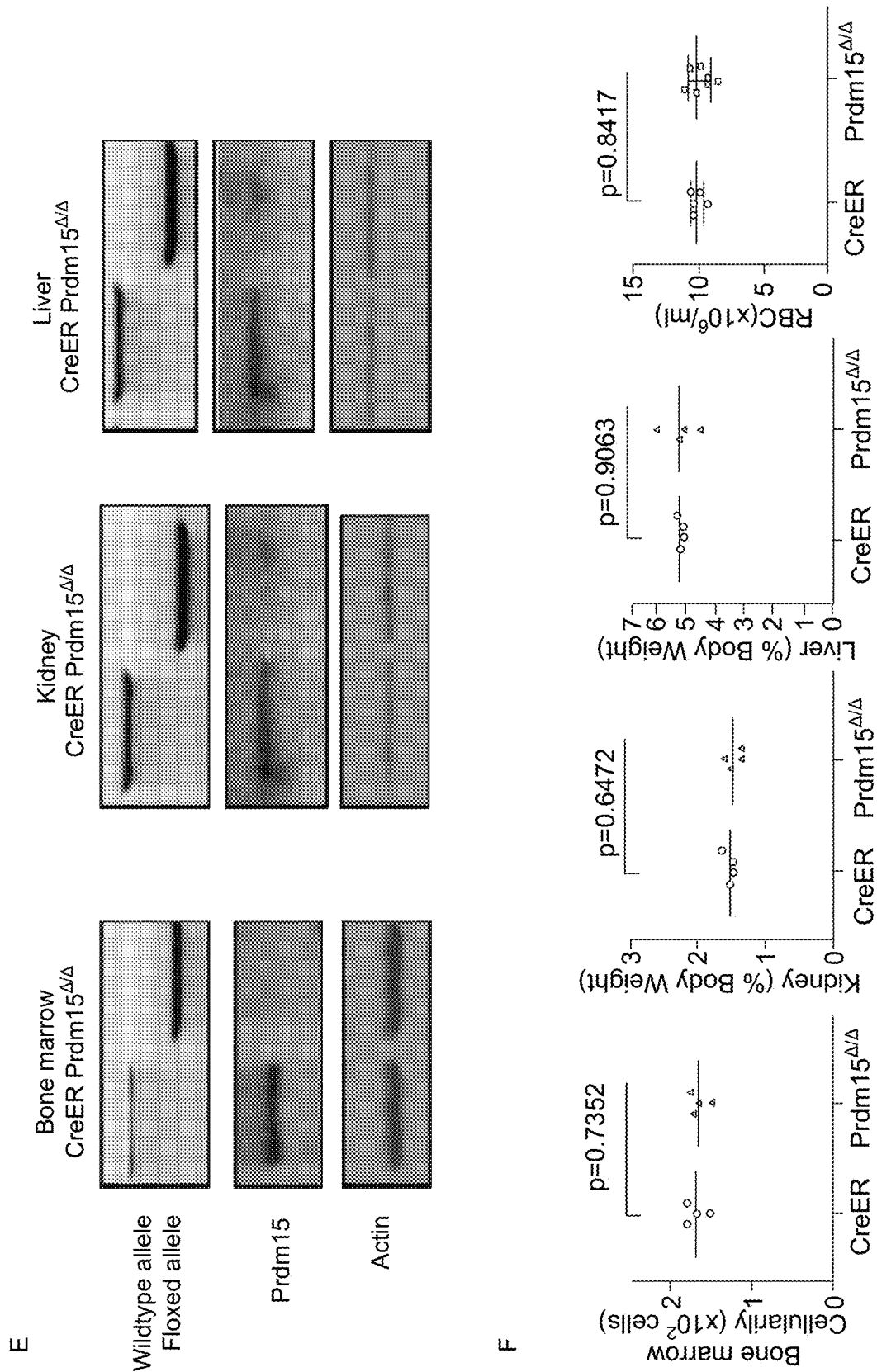
Figure 2:
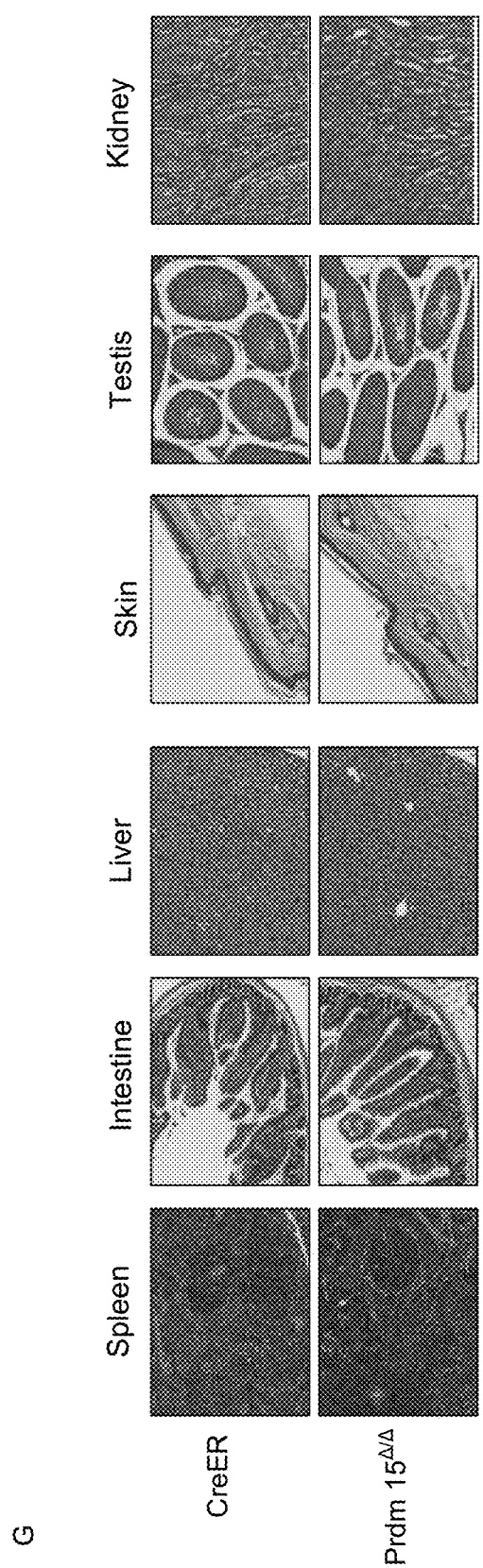

FIG. 2 PRDM15 is dispensable for tissue homeostasis in adult mice. A. Western blot showing the presence of PRDM15 protein in various adult mouse tissues. B. Schematic of the Prdm15 'knockout-first' conditional allele (adapted from: (www.mousephenot.ype.org/about ikmrn/eucmm-prgram/eucomm-targeting-strategies) C. Survival curve of Rosa26;CreERT2 (CreER) or PRDM15$^{F/F}$;Rosa26;CreERT2 (PRDM15$^{F/F}$;CreER) mice that were injected with tamoxifen at 8-weeks of age to generate PRDM15$^{\Delta/\Delta}$ mice. D. Weights of 4-month-old CreER and PRDM15$^{\Delta/\Delta}$; CreER mice that were injected with tamoxfen at 8-weeks of age. E. (upper panel) Agarose gel electrophoresis showing the wild-type or floxed allele of Prdm15 and (lower panel) Western blot showing the expression of PRDM15 and actin in various organs from the mice described in (D). F. Bone marrow cellularity and organ weights of mice described in (C). G. H&E images of various organs from the mice described in (C).

Figure 3:
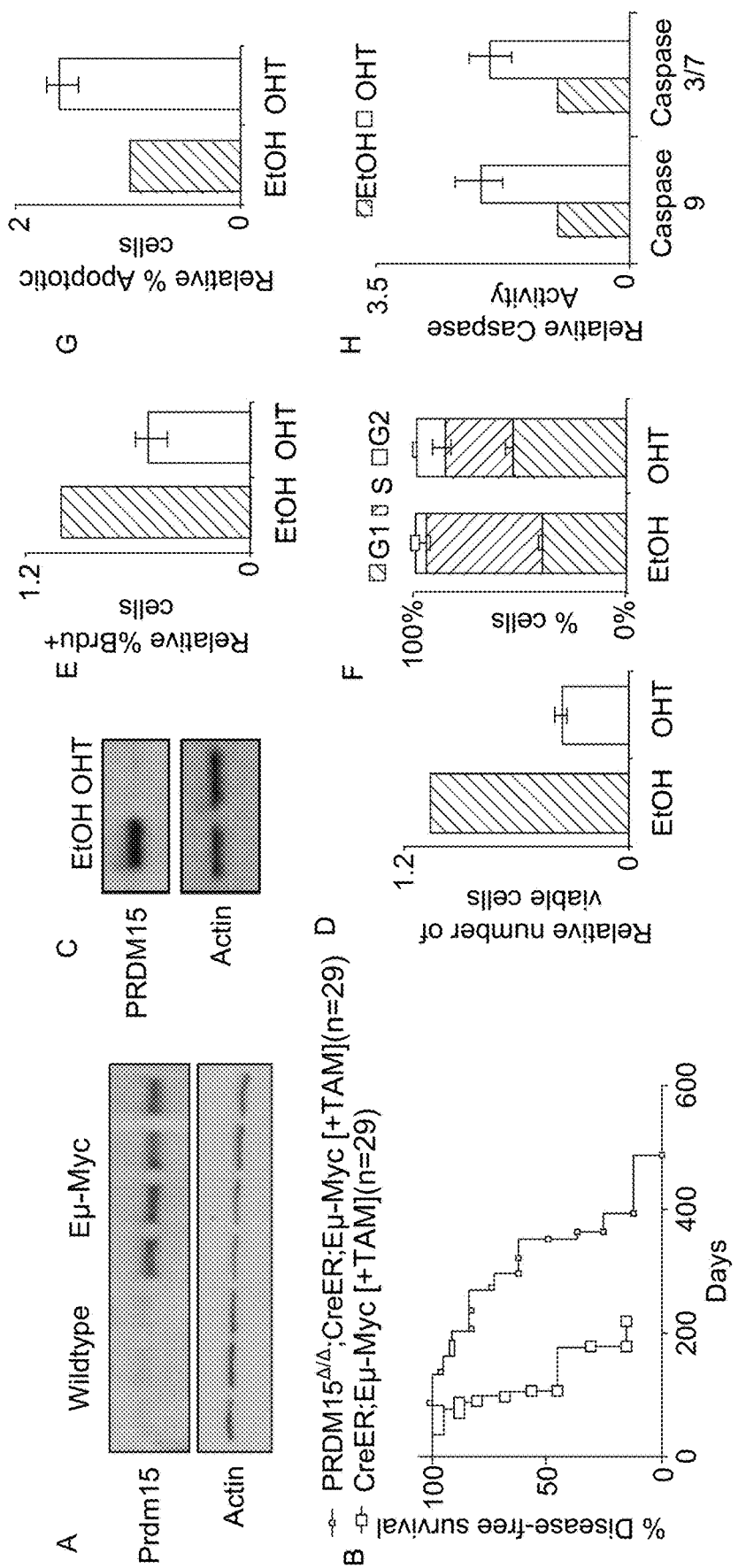

FIG. 3 PRDM15 is essential for lymphoma initiation in the EmuMyc mouse model A. Western blot showing the expression of PRDM15 in bone marrow-derived B cells from wildtype or Eµ-Myc mice. B. Disease-free survival of CreER;Eµ-Myc or PRDM15$^{F/F}$;CreER;Eµ-Myc mice that were injected with tamoxifen at 5-weeks of age. C. B cells were isolated from the bone marrow of PRDM15$^{F/F}$;CreER; Eµ-Myc and cultured in vitro. 4-OHT was added to induce PRDM15 deletion. The western blot validates the absence of PRDM15 protein following OHT addition. D. The number of viable cells, measured by Cell Titer Glo Cell Luminescence ATP assay, following PRDM15 deletion. E. The cells were labeled with BrdU and BrdU incorporation was assessed by FACS. F. Cell cycle analysis was determined by FACS based on BrdU incorporation and PI staining. G. Apoptosis was determined by FACS. H. Caspase 3/7 activity was measured by Caspase Glo Assay.

Figure 4:
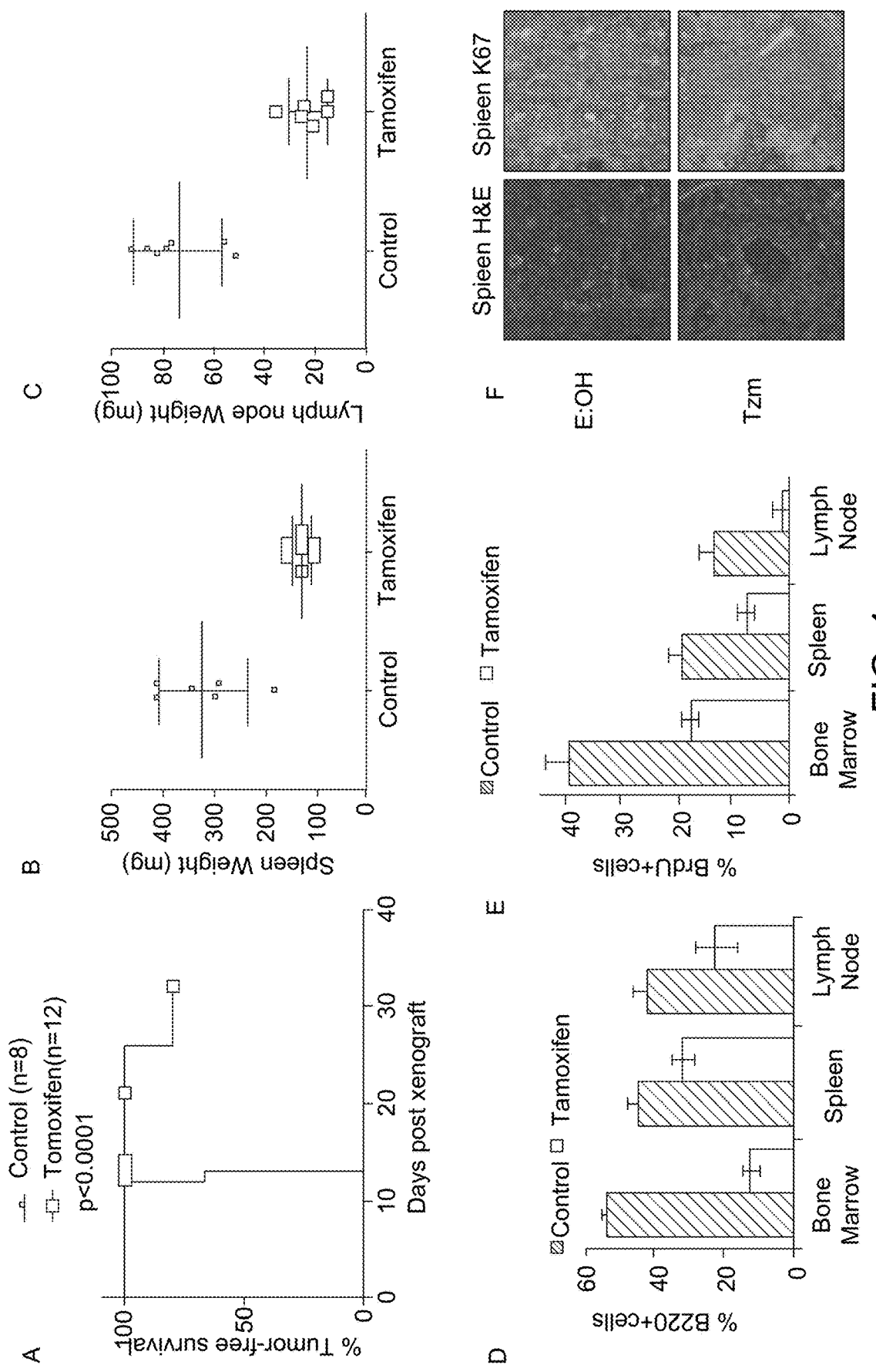

FIG. 4 PRDM15 is essential for lymphoma maintenance in the Eµ>Myc mouse model (A) Overall tumour free survival of mice transplanted with PRDM15$^{F/F}$;CreER;Eµ-Myc lymphoma cells, and injected with EtOH or Tamoxifen 1 week later. The weights of spleens (B) and lymph nodes (C) of mice transplanted with PRDM15$^{F/F}$;CreER;Eµ-Myc lymphoma cells, and injected with EtOH or Tamoxifen 1 week later. The mice were sacrificed when the control (EtOH) mice started to display signs of disease. The percentage of B220+(D) and BrdU(E) cells in the spleen, lymph nodes and bone marrow of the mice described above. (F) H&E staining and immunohistochemistry for Ki67 on spleen sections from the mice are described herein.

Figure 5:
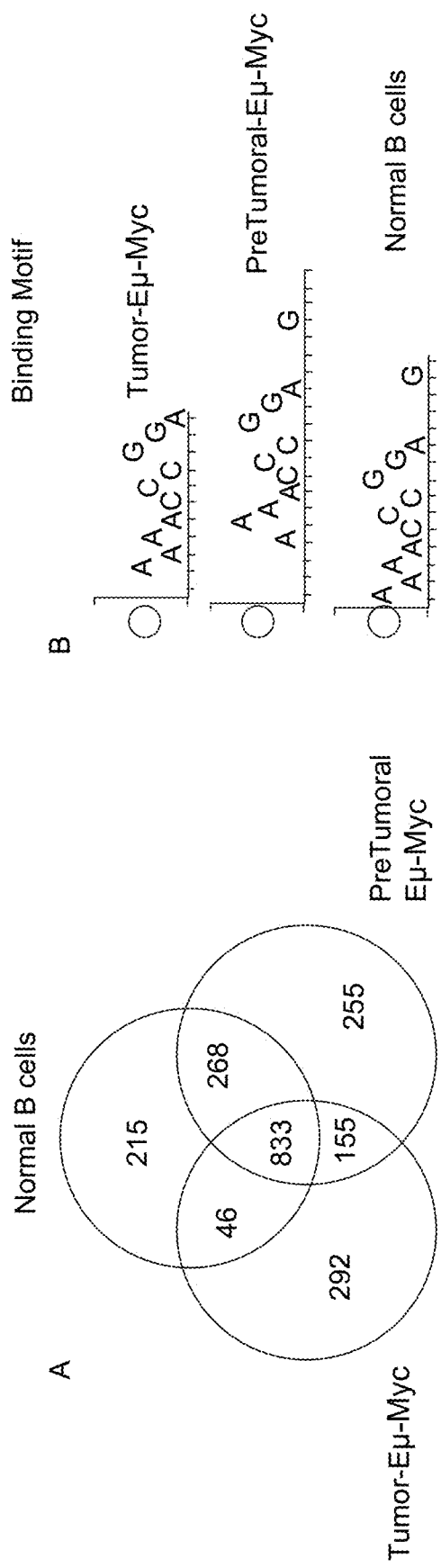

FIG. 5 Genomewide Identification of PRDM15 targets A. Overlap of PRDM15 binding sites in WT B cells, Pre TumouralE-Myc B cells and El-Myc Tumours. B. Motif bound by PRMD15 in vivo in the three different cell types.

Figure 6:
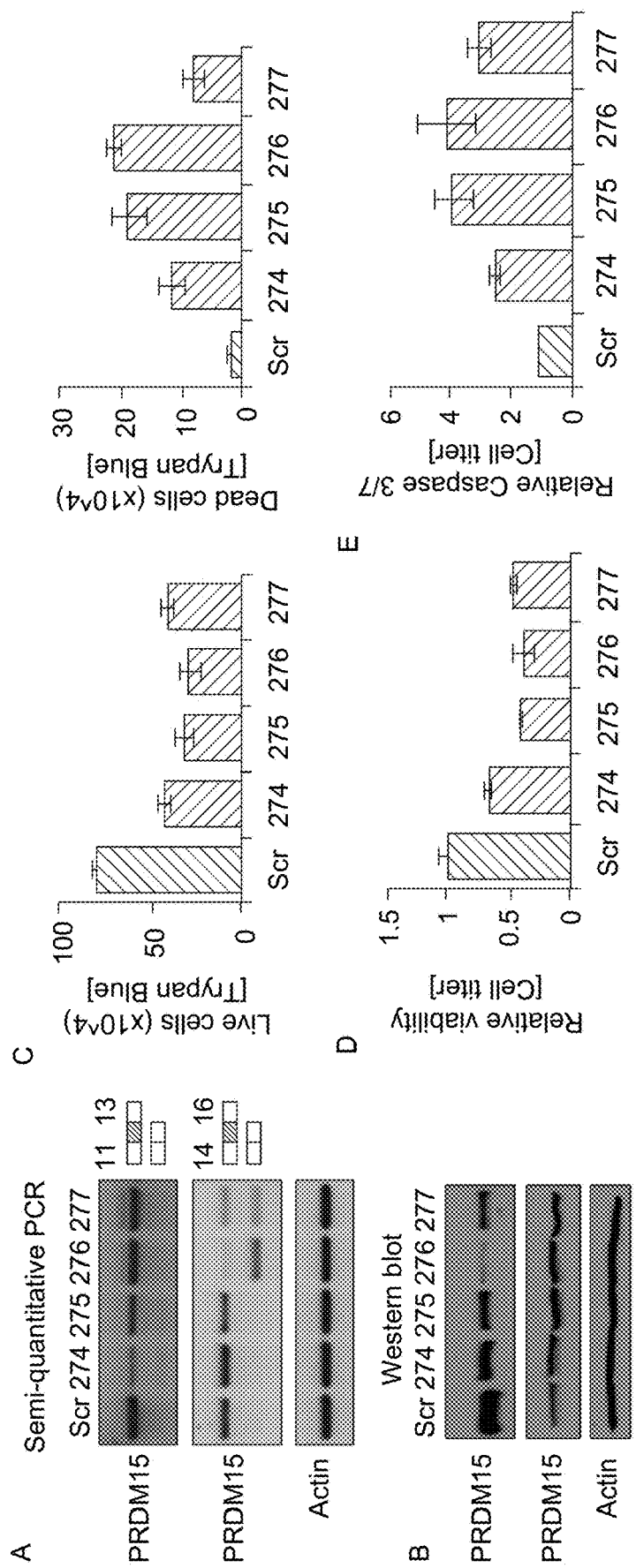

FIG. 6 A. Antisense oligonucleotide (ASO) design to induce exon skipping of PRDM15 premRNA in vitro. A-B. Titration of PRDM15 ASOs. Cells were transfected with different ASOs at a fix concentration of 100 nM. RNA was collected and the efficacy of exon skipping was measured by: A. semi-quantitative PCR and running the products on a gel. The forward and reverse primers were designed on Exons 11-13 (top panel, to validate ASO #274 and ASO #275) and 14-16 (middle panel, to validate ASO #276 and ASO #277), respectively, so as to amplify a longer isoform (normal) and a shorter isoform (generated by exon skipping induced by PRDM15-ASO) lacking exon 12 (ASO #274 and ASO #275) and 15 (ASO #276 and ASO #277). B. Validation of reduction in PRDM15 protein levels by Western blotting. PRMT5, an unrelated chromatin modifier, is used as a control for specificity and loading control (together with Actin). C-E Phenotypic effects in vivo following PRDM15 ASO treatment C. Live and dead cell quantification by trypan blue; D. Relative viability and E. relative Caspase 3/7 activity in DLBCL Patient Derived Cells, 3 days following electroporation with the respective ASOs.

Figure 7:
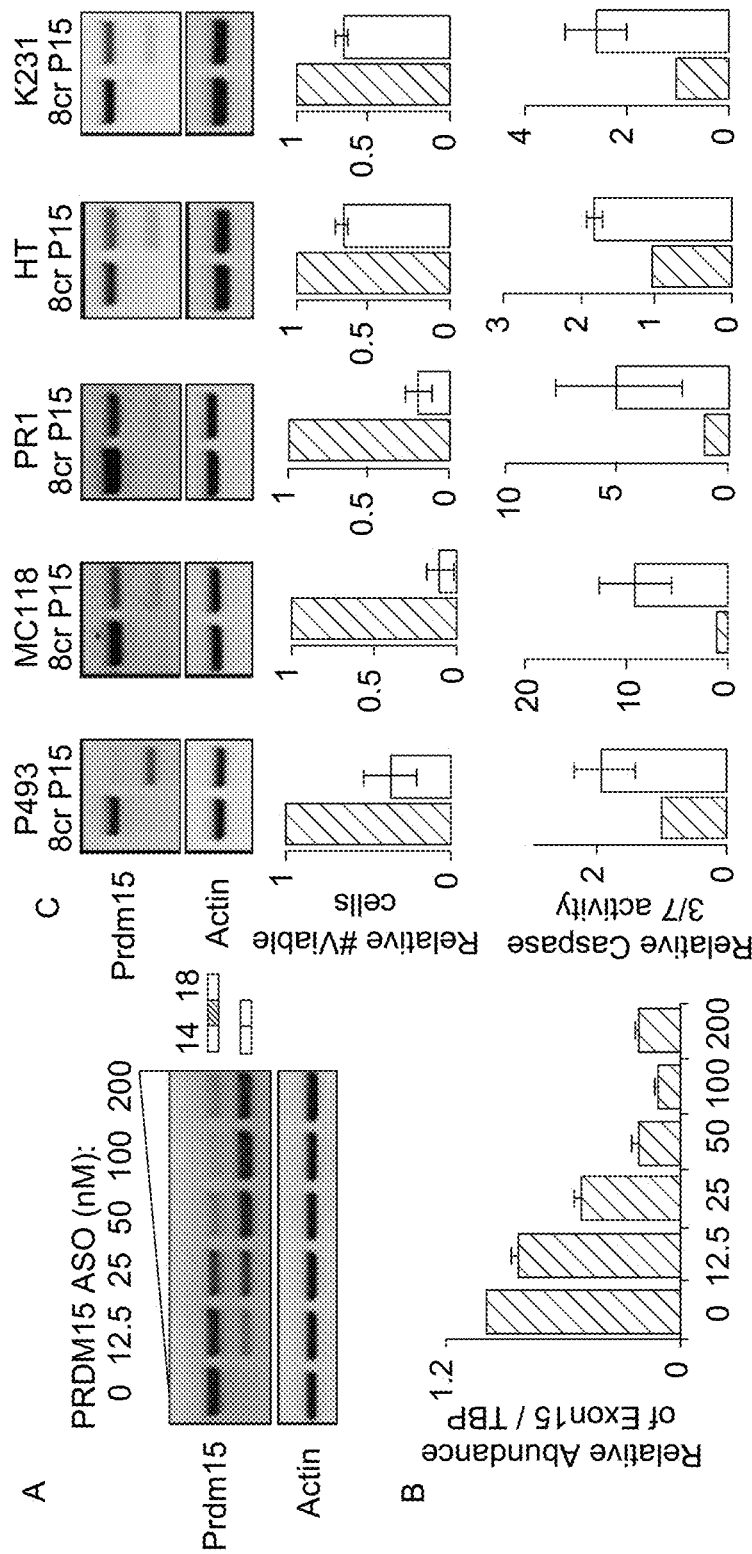
Figure 7:
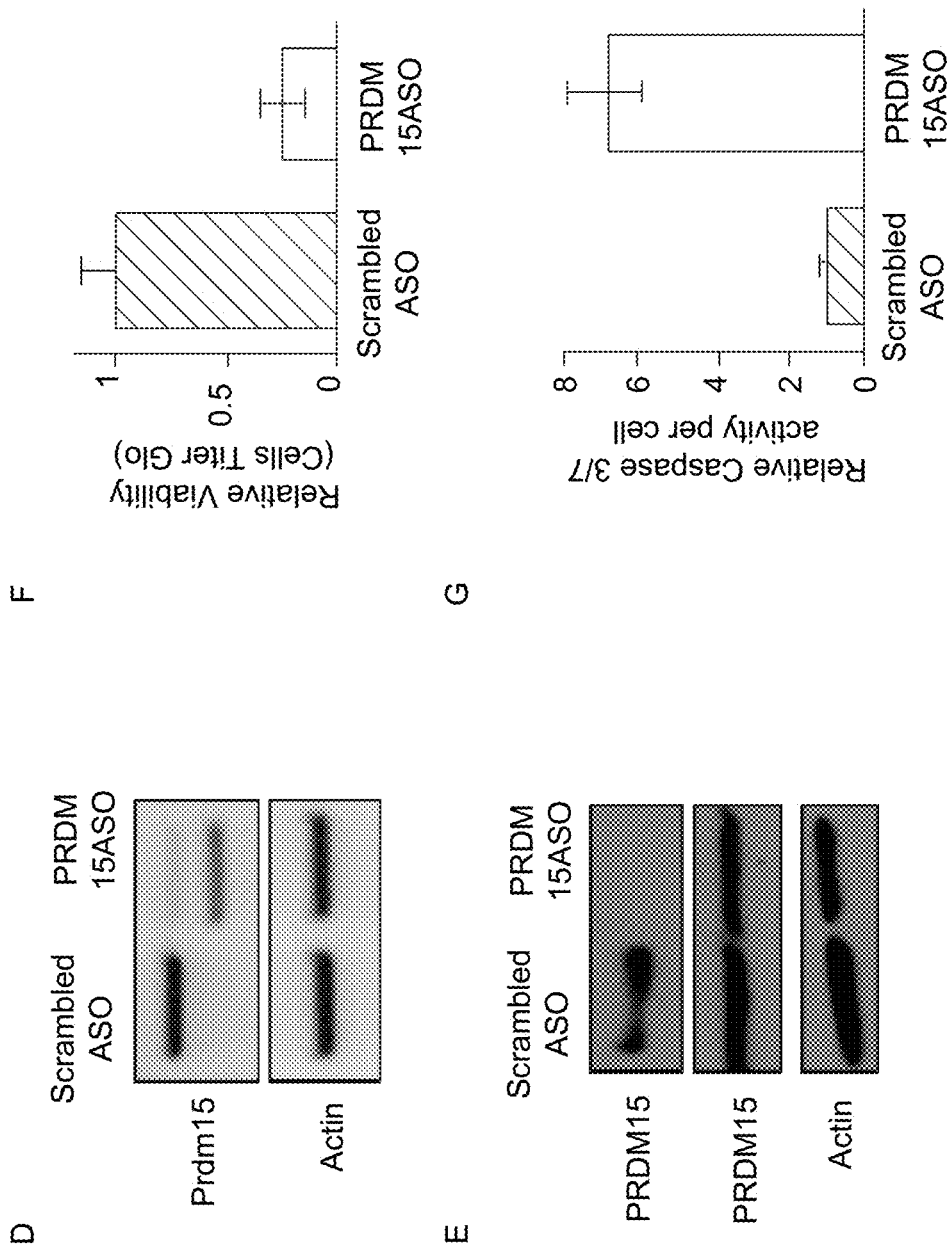

FIG. 7 A. Antisense oligonucleotide (ASO) design to induce exon skipping of PRDM15 pre-mRNA in vitro. A-B. Titration of PRDM15 ASO. Cells were transfected with the indicated amounts of ASO. RNA was collected and the efficacy of exon skipping was measured by: A. semi-quantitative PCR and running the products on a gel. The forward and reverse primers were designed on Exons 14 and 16, respectively, so as to amplify a longer isoform (normal) containing exons 14, 15 and 16, and a shorter isoform (generated by exon skipping induced by PRDM15-ASO) lacking exon 15. B. Relative abundance of PRDM15 exon 15, relative to TBP, measured by quantitative real-time PCR. C. Human Lymphoma cell lines were transfected with the indicated ASO (Scr=Scrambles Control; P15=PRDM15 ASO). RNA was collected and the efficacy of exon skipping was measured by semi-quantitative PCR. The forward and reverse primers were designed on Exons 14 and 16, respectively, so as to amplify a longer isoform (top band) containing exons 14, 15 and 16, and a shorter isoform (generated by exon skipping induced by PRDM15-ASO) lacking exon 15. Actin is used as a loading control. Bottom panels. Viability and Caspase 3/7 activation (apoptosis) are quantified C-E. Therapeutic efficacy of PRDM15 ASO in lymphoma treatment in vitro. C. Primary diffuse large B cell lymphoma cells were obtained from a patient, and electroporated with either Scramble or PRDM15-ASO. Validation of ASO efficacy by semi-quantitative PCR. D. Validation of reduction in PRDM15 protein levels by Western blotting. Prmt5, an unrelated chromatin modifier, is used as a control for specificity and loading control (together with Actin). E-F. Relative viability and relative Caspase 3/7 activity in DLBCL Patient Derived Cells, 3 days following electroporation with the respective ASOs.

Figure 8:
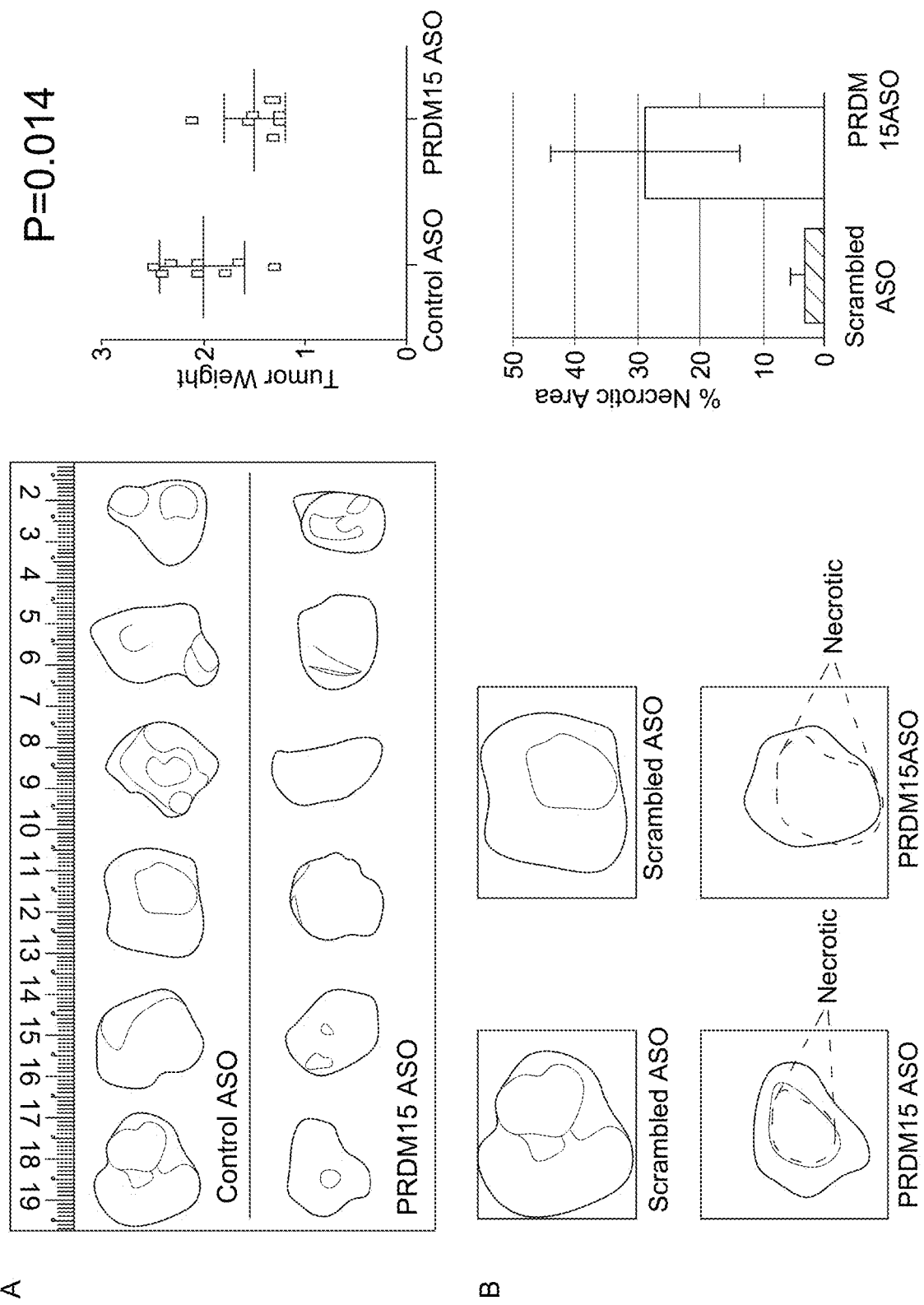

FIG. 8. Antisense oligonucleotide (ASO) design to induce exon skipping of PRDM15 pre-mRNA in vivo. A. Cohorts of PDX model of DLBCL (BCL13) were established. When tumors reached 150-250 mm$^3$ of average volume, cohorts were treated with either PRDM15 ASO or control srambled intratumorally every 2 days. Tumor size was assessed at day 21. Data represent the mean (±SEM) of the different biological replicates. B. The necrotic portion of the tumor was evaluated by histological analysis and quantified (right panel).

Figure 9:
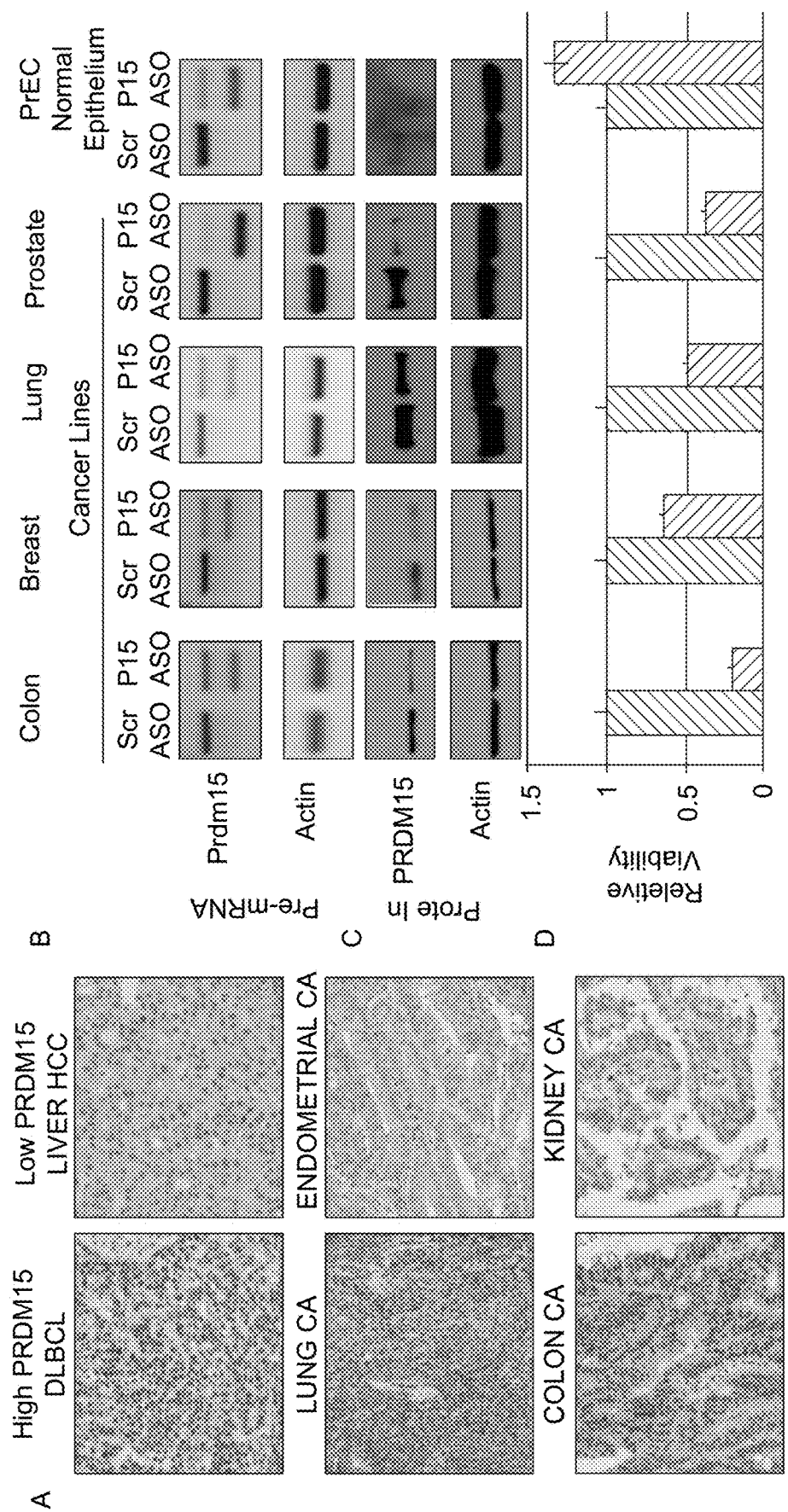

FIG. 9 A. Examples of TMA stained for PRDM15. Left Column. Tumor types expressing high level of nuclear PRDM15 (DLBCL, Lung and Colon Cancer. Right Column. Tumor types expressing low levels or no PRDM15 (Liver Hepatocellular Carcinoma HCC, Endometrial and Kidney Carcinomas). A-D Human Colon (HCT116), Breast (MDA453), Lung (A357) and Prostate (PC3) lines were transfected with the indicated ASO (Scr=Scrambles Control; P15=PRDM15 ASO). A control normal prostate epithelium line (PrEC) is used to demonstrate that PRDM15 is expressed at lower protein levels and is dispensable for cell survival. B. RNA was collected and the efficacy of exon skipping was measured by semi-quantitative PCR. The forward and reverse primers were designed on Exons 14 and 16, respectively, so as to amplify a longer isoform (top band) containing exons 14, 15 and 16, and a shorter isoform (generated by exon skipping induced by PRDM15-ASO) lacking exon 15. Actin is used as a loading control. C. Western blot for PRDM15, Actin and PRMT5. D. Relative Viability quantified with cell titer glo kit.

PRDM15 is a very promising anti-cancer therapeutic target. We have identified PRDM15 as a protein important during embryonic development, but dispensable for normal adult tissue homeostasis. PRDM15 is under direct transcriptional control of the oncogene MYC, and we show that it is aberrantly overexpressed in a variety of murine and human cancers. PRDM15 belongs to a family of putative methyltransferases, so it is potentially targetable by small molecule inhibitors.

To date however we have not identified a relevant substrate. We thus reasoned that targeting directly PRDM15 pre-mRNA, would be an ideal strategy to reduce PRDM15 protein levels and selectively affect tumor growth. Our strategy is not only easier to achieve pharmacologically (and therefore faster to introduce into the clinic), but may additionally have broader and more robust antitumor effects, as this would inhibit both catalytic dependent and independent (scaffolding) functions of PRDM15.

The non-sense mediated decay (NMD) pathway eliminates mRNAs with premature termination codons. We reasoned that we could exploit this cellular machinery to induce aberrant splicing of the PRDM15 pre-mRNA, targeting it to NMD. We propose the use of splice-switching, NMD-targeting, ASOs as a therapeutic approach to PRDM15 targeting. We provide evidence that this clinically-compatible strategy has robust antitumor effects and is applicable to a wide range of human tumors (namely, PRDM15-expressing cancers).

It is an object of the invention to provide direct and selective inhibitors of PRDM15 for use in treatment of cancer. With direct, it is meant that PRDM15 is directly targeted (i.e. the PRDM15 protein abundance is affected). With selective, it is meant that the inhibitors specifically inhibit PRDM15, and do not inhibit any other PRDM family members. This is important to prevent deleterious side effects (i.e. iatrogenic effects caused by the therapy), given that several PRDM family members have tumor suppressor activity in a variety of cancers.

This is equivalent as saying that methods of treating cancer in a subject in need thereof are provided, comprising a step of administering a direct and selective inhibitor of PRDM15 to said subject.

According to particular embodiments, the cancer has high levels of PRDM15 protein (i.e., is an PRDM15 overexpressing cancer). It is noteworthy that PRDM15 is either not expressed, or expressed at very low levels in adult tissues. Overexpression in cancer cells can thus be simply detectable expression of PRDM15 protein.

According to particular embodiments, overexpression of PRDM15 means that PRDM15 protein is readily detectable by immunohistochemistry (IHC) and/or Western blotting.

According to particular embodiments, the cancer is selected from the group of hematological malignancies (lymphomas and leukemias), lung cancer, breast cancer, prostate cancer, stomach cancer, testis cancer, larynx cancer, liver cancer, uterus cancer, colorectal cancer, melanoma, glioblastoma, osteosarcoma and retinoblastoma. According to more particular embodiments, the cancer is B cell lymphomas (Follicular, Diffuse Large B cells Lymphomas).

Although any direct and selective inhibitor of PRDM15 can be suitable for the methods taught herein, it is particularly envisaged that the PRDM15 inhibitor acts at the RNA level. More particularly, the inhibitor is an antisense oligonucleotide (ASO). The antisense oligonucleotides should affect PRDM15 expression, e.g. by inducing PRDM15 RNA degradation. Even more particularly envisaged is an antisense oligonucleotide that induces exon skipping. Most particularly, the exon that is skipped is exon 12 or exon 15.

Accordingly, also provided herein are PRDM15 antisense oligonucleotides that induce exon skipping in the PRDM15 transcript. Particularly, PRDM15 antisense oligonucleotides that induce skipping of exon 12 or exon 15 (FIG. 1). Such antisense oligonucleotides are also provided for use as a medicament. Particularly, they are provided for treatment of cancer (such as e.g. hematological malignancies (lymphomas and leukemias), lung cancer, breast cancer, prostate cancer, stomach cancer, testis cancer, larynx cancer, liver cancer, uterus cancer, colorectal cancer, melanoma, glioblastoma, osteosarcoma and retinoblastoma).

The PRDM15 inhibitor may be administered as a single agent, or simultaneously with other agents (e.g. chemotherapeutic).

DEFINITIONS

The present invention will be described with respect to particular embodiments and with reference to certain drawings, but the invention is not limited thereto but only by the claims.

Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, New York (1989); and Ausubel et al., Current Protocols in Molecular Biology (Supplement 47), John Wiley & Sons, New York (1999), for definitions and terms of the art.

The definitions provided herein should not be construed to have a scope less than understood by a person of ordinary skill in the art.

As used herein, "PRDM15" refers to the PRDM15 gene (Gene ID: 63977 in humans; ID: 114604 in mouse), also known as C21orf83, PFM15, ZNF298) or protein encoded thereby. The gene encodes a Zn Finger nuclear protein that contains a PR domain at the N-terminus.

Example 1

PRDM15 is Dispensable for Adult Mouse Homeostasis

We profiled the expression of PRDM15 in adult mouse tissues and found that it is ubiquitously expressed in various major organs (spleen, bone marrow, liver, kidneys) (FIG. 2A).

To investigate the role of Prdm15 in physiological and pathological conditions in vivo, we generated a knockout-first mouse model[25] (original construct from the EUCOMM consortium (European Conditional Mouse Mutagenesis program) (FIG. 2B). The presence of a splice acceptor lacZ cassette in intron 3 of the Prdm15$^{ac}$z allele prevents the production of a functional PRDM15 protein. To generate the Prdm15 conditional allele, we crossed Prdm15$^{lacz/+}$ and flippase (FLPe)-expressing mice to excise the lacZ cassette. The resulting Prdm15 conditional allele contains loxP sites that flank exon 4 (designated as Prdm15$^F$) (FIG. 2B). Using a tamoxifen-inducible KO model for PRMD15 (PRDM15$^{F/F}$; Rosa26Cre-ERT2-subsequently referred to as PRDM15$^{F/F}$; CreER or $^{F/F}$ for short), we systemically deleted PRDM15 in the whole body (referred to as PRDM15$^{\Delta/\Delta}$; CreER or $^{\Delta/\Delta}$ for short). Given concerns in the literature about non-specific Cre-mediated toxicity, we used Rosa26;Cre-ERT2 (subsequently referred to as CreER) mice, with no floxed allele, as controls. Both groups were injected intraperitoneally (IP) with tamoxifen when they were 8-weeks-old in order to activate the Cre recombinase, resulting in control PRDM15 wt (CreER) or PRDM15 null (PRDM15$^{\Delta/\Delta}$; CreER) mice.

We have been observing the resultant PRDM15$^{\Delta/\Delta}$ mice for over 18 months now, and we do not observe any adverse phenotype (FIG. 2C). At 2 months following tamoxifen administration, the CreER and PRDM15$^{\Delta/\Delta}$;CreER mice were of similar weights (FIG. 2D). We validated that PRDM15 deletion in vivo was indeed efficient using PCR primers designed to differentiate between the wild type and floxed alleles from genomic DNA (FIG. 2E upper panel) and by western blotting to assess PRDM15 protein levels (FIG. 2E lower panels). The mice had similar organ sizes, bone marrow cellularity and red blood cell counts (FIG. 2F).

Furthermore, histological analysis did not reveal any overt differences between various tissues from the mice (FIG. 2G).

These data demonstrate that in adult mice, PRDM15 is dispensable for normal tissue homeostasis, which is in striking contrast to its essential functions during early embryonic development (Guccione and Mzoughi unpublished).

Example 2

PRMD15 is a Novel Oncoqene in Myc-Driven Lymphomas

We observed that PRDM15 was overexpressed in bone marrow B cells obtained from Eµ-Myc mice, compared to that from wild type mice, suggesting a potential oncogenic function for PRDM15 (FIG. 3A). As such, we crossed the CreER control mice and PRDM15$^{F/F}$; CreER mice onto the Eµ-Myc background to obtain CreER;Eµ-Myc and PRDM15$^{F/F}$; CreER;Eµ-Myc mice.

These transgenic mice develop B cell lymphomas driven by MYC, and the conditionality of the model enables us to temporally delete PRDM15 at various stages of tumour development.

PRDM15 is Necessary for Tumour Initiation

To assess the role of PRDM15 in tumour initiation, pretumoural (5-week-old) CreER;Eµ-Myc and PRDM15$^{F/F}$; CreER;Eµ-Myc mice were injected with tamoxifen and monitored for disease-free survival. We found a striking delay in disease onset, with the PRDM15$^{\Delta/\Delta}$; CreER;Eµ-Myc mice having a median disease-free survival of 354 days, compared to 109 days for the control CreER;Eµ-Myc mice (FIG. 3B).

Next, we isolated primary B cells from PRDM15$^{F/F}$; CreER;Eµ-Myc mice to study the effects of the acute deletion of PRDM15 in vitro, as well as to ascertain if the delay in lymphomagenesis observed in FIG. 3B was a cell autonomous function of PRDM15. In vitro, PRDM15 deletion can be achieved efficiently by the addition of 4-OHT in the cell culture media, as shown by the absence of detectable PRDM15 protein by western blot (FIG. 3C). Acute PRDM15 deletion resulted in a decrease in the number of viable cells (FIG. 3D), and this was associated with a reduction in DNA synthesis/proliferation (reduction in the number of BrdU positive cells) (FIG. 3E), as well as an increase in the number of cells in G1 and G2/M (FIG. 3F). Furthermore, PRDM15 depletion caused a significant increase in apoptosis (FIG. 3G), which was caspase dependent, with increased activity of caspase 9 and caspase 3/7 observed (FIG. 3H).

PRDM15 is Necessary for Tumour Maintenance

To assess the role of PRDM15 in tumour maintenance, primary tumours were isolated from tumour-bearing PRDM15$^{F/F}$;CreER;Eµ-Myc mice and transplanted into syngeneic recipient mice.

At 7 days following transplant, the recipient mice were injected with either EtOH (vehicle control) or tamoxifen, to deplete PRDM15. As shown in FIG. 4A all control mice had palpable tumors by day 12, while none of the TAM treated mice had any. At this stage (day 12) we sacrificed 6 mice from both groups (all controls were sick). Mice with PRDM15-depleted tumors had significantly lower disease burden than the control group, as determined by their spleen (FIG. 4B) and lymph node (FIG. 4C) weights. By FACS analysis, we confirmed that the bone marrow, spleens and lymph nodes of the tamoxifen-injected mice had a lower percentage of B cells (B220+) than the control mice (FIG. 4D). Additionally, prior to sacrifice, the mice were injected with a pulse of BrdU, and we found that the cells in the bone marrow, spleens and lymph nodes of the tamoxifen-injected mice were significantly less proliferative than those in the control mice (FIG. 4E). Representative histological pictures of the spleens of the control and tamoxifen-injected mice are shown (FIG. 4F).

Example 3

Genomewide Identification of PRDM15 Targets:

PRDM15 contains multiple zinc finger-DNA binding domains at its carboxyl terminus. We tested (preliminary run to test feasibility) whether PRDM15 would directly bind to DNA by performing Chip-sequencing analysis on B cells derived from different stages of Myc-driven tumour development. PRDM15 binds to about 1000 sites in both normal B cells and pretumoural and tumoural Eµ-Myc cells (FIG. 5A). De novo motif analysis identifies a clear consensus binding-site for PRDM15 (FIG. 5B), which is remarkably similar to the one identified in mouse Embryonic Stem Cells (Mzoughi and Guccione, unpublished).

Example 4

Targeting PRDM15 in Human Lymphomas with Antisense Oligonucleotides In Vitro and In Vivo.

We have previously demonstrated the potential utility of antisense oligonucleotides (ASOs) as a means to effectively and specifically reduce the expression of a target protein, by affecting the stability of its pre-mRNA. Specifically, we designed ASOs to induce exon skipping or intron retention of pre-mRNA transcripts (e.g. Mdm4, Ep400, Dv/1), which results in the generation of a pre-termination codon or a frameshift, leading to nonsense-mediated decay and the subsequent reduction in protein levels[26,27]. Importantly we have proven the efficacy of our approach in PDX models of melanoma and DLBCL[26], and novel generation ASOs are effective as single agents in preclinical and clinical models of follicular and DLBC Lymphomas, following intravenous administration[28].

Here, our antisense oligonucleotide was designed to induce the skipping of PRDM15 exon 15 (ASO #276 and ASO #277) or PRDM15 exon 12 (ASO #274 and ASO #275), respectively (FIG. 6).

We did further testing on ASO #276 to assess its $IC_{50}$=25 nM (FIG. 6A-B) Next we assessed the efficacy in 4 DLBCL cell lines (FIG. 6C) and in a primary, triple hit, patient-derived diffuse large B cell lymphoma (TH DLBCL with MYC+, and translocations of both BCL2 and BCL6). The PRDM15 ASO efficiently caused the skipping of exon 15 (FIG. 6D), and consequently, reduction in PRDM15 protein levels (FIG. 6E). Importantly, this was highly specific, and did not affect the levels of the housekeeping protein, Actin, or another tested protein, PRMT5 (FIG. 6E). In these primary DLBCL cells, the depletion of PRDM15 protein by means of antisense oligonucleotide-mediated exon skipping profoundly reduced cell viability (FIG. 6F). This was accompanied by a significant increase in Caspase 3/7 activity, suggesting apoptosis (FIG. 6G).

The same PRDM15 ASO, when injected intratumorally in 5 independent animals, induced a reduction in tumor size, and most importantly a strong induction of necrosis (ranging between 11-50% of the infiltrated tissue) in all TH DLBCL PDX tested, when compared to control (ranging between 0-6% of necrosis) (FIG. 8A-B).

Finally, we stained several tumor tissue samples for PRDM15 [by IHC, ImmunoHistoChemistry](FIG. 9A). Lung and Colon cancer expressed very high level of nuclear PRDM15, while levels of PRMD15 appear lower in liver, endometrial and kidney carcinomas. To assess the relevance of PRDM15 in sustaining cancer growth in these tumor types we tested the effect of PRDM15-ASO treatment on representative cell lines. We induced efficient exon skipping in all cell lines tested (FIG. 9B). Remarkably we observed a reduction in protein levels (FIG. 9C) and in viability of all cancer lines tested (FIG. 9D)[Human Colon (HCT116), Breast (MDA453), Lung (A357) and Prostate (PC3) lines], but not for a normal prostate epithelium cell line (PrEC) (FIG. 9D right bars).

Methods

```
ASO #274:
                                        (SEQ ID NO: 18)
UUG GAG GUG UCG AAG CAC ACG GGG UG (SEQ ID NO: 92)
[mU]*[mU]*[mG]*[mG]*[mA]*[mG]*[mG]*[mU]*[mG]*[mU]*

[mC]*[mG]*[mA]*[mA]*[mG]*[mC]*[mA]*[mC]*[mA]*[mC]*

[mG]*[mG]*[mG]*[mG]*[mU]*[mG]*

ASO #275:
                                        (SEQ ID NO: 19)
UCA UCC AGU UGC AGU CAU CCU CGU U (SEQ ID NO: 93)
[mU]*[mC]*[mA]*[mU]*[mC]*[mC]*[mA]*[mG]*[mU]*[mU]*

[mG]*[mC]*[mA]*[mG]*[mU]*[mC]*[mA]*[mU]*[mC]*[mC]*

[mU]*[mC]*[mG]*[mU]*[mU]*

ASO #276:
                                        (SEQ ID NO: 26)
ACU CAC AGG CUC AUC CGG AGG GAC (SEQ ID NO: 94)
[mA]*[mC]*[mU]*[mC]*[mA]*[mC]*[mA]*[mG]*[mG]*[mC]*

[mU]*[mC]*[mA]*[mU]*[mC]*[mC]*[mG]*[mG]*[mA]*[mG]*

[mG]*[mG]*[mA]*[mC]*

ASO #277:
                                        (SEQ ID NO: 27)
GGA CCU CGG UAA UGA UCU CUG CCA CUU GC (SEQ ID NO: 95)
[mG]*[mG]*[mA]*[mC]*[mC]*[mU]*[mC]*[mG]*[mG]*[mU]*

[mA]*[mA]*[mU]*[mG]*[mA]*[mU]*[mC]*[mU]*[mC]*[mU]*

[mG]*[mC]*[mC]*[mA]*[mC]*[mU]*[mU]*[mG]*[mC]*
* = PHOSPHOROTHIOATE LINKAGE
[mA], [mU], [mG], [mC] = 2'O-METHYL RNA
```

DLBCL PDX

All the procedures were approved and carried out in accordance with the guiding ethical principles of the Institutional review board (SGH). Written informed consent was obtained for use of these samples for the specific research purpose only. The tumor sample used for constructing the DLBCL xenograft was obtained from a 53 year old man with a past history of Stage I diffuse large B-cell lymphoma 10 years earlier and was treated with CHOP (cyclophosphamide, doxorubicin, vincristine, prednisolone) chemotherapy with complete remission. He presented to our hospital with relapsed disease in the bone marrow, leptomeninges and pleural effusions. He was treated with 2 courses of RICE (rituximab, ifosfamide, carboplatin, etoposide) and intrathecal methotrexate/cytarabine, then 4 courses of DHAP (dexamethasone, cytarabine, cisplatin) and intrathecal methotrexate but disease continued to progress and the patient died a year after disease relapse. Cytological examination of the pleural fluid showed discohesive lymphomatous population featuring large cells with vesicular chromatin and conspicuous nucleoli. Neoplastic cells expressed pan-B markers (PAX5, CD20, CD22, CD79a), with aberrant expression of CD5, strong expression of bcl2 and a high proliferation fraction of 70-80%. Neoplastic lymphocytes display a nongerminal centre phenotype (CD10-, bcl6+, MUM1+, FOXP1+) but staining for c-myc was low at 20%. Interphase fluorescence in situ hybridization showed gains of BCL2 and rearrangements of BCL6 and IGH genes, whereas normal patterns were seen for C-MYC.

Xenograft construction and treatment: The pleural fluid was collected in cold sterile 20% RPMI 1640 medium. Neoplastic cells in the pleural fluid were isolated with Ficoll-Paque PLUS (GE Healthcare, OH), and subsequently resuspended in RPMI 160 medium (Life Technologies, CA) with 20% Fetal Bovine Serum (Life Technologies, CA). A representative part of the tumor sample was fixed in 10% Neutral Buffered Formalin and the other part was utilised for xenotransplantation. The cell suspension was then implanted subcutaneously to 4-6 week old NOD scid mice. The tumors were monitored periodically and allowed to establish and grow to a maximum of 1000 mm3. The mice were then sacrificed, tumors were harvested and general necropsy was performed. Xenograft tumors were immediately fresh-frozen, formalin-fixed, stored in 90% FBS and 10% DMSO or placed in RPMI 160 medium. This process was repeated to produce subsequent generations of PDX models (P2, P3, P4, . . . ). To evaluate the maintenance of the morphology and main characteristics of the tumor of origin, formalin-fixed, paraffin-embedded (FFPE) tissues sections from patient tumor samples and xenografts of all established Patient derived xenograft models were stained with hematoxylin and eosin (H&E). In addition these sections were also immunostained to determine the expression of various markers. All these slides were individually observed and reviewed by a clinical pathologist. For the current study, tumor fragments (approximately 50 mg, P4) were implanted subcutaneously onto the flank of female NOD scid (4-6 weeks) mice. Tumors were allowed to grow for about 150-250 mm3. The animals were randomized into two different groups (n=5) as mentioned below Group-I-Scrambled Vivo-Morpholinos (GeneToolslnc) (Dose 25 µL, intratumorally) Group-II-exon 6 targeting Vivo-Morpholinos (GeneToolslnc) (Dose 25 µL, intratumorally) Animals were monitored regularly and body weight was measured every day during the treatment period. At the end of the treatment period all the animals were sacrificed, tumors were removed, weighed and observed for gross pathology. Each piece was then divided into two parts. One piece of the tumor was fixed in 10% NBF for 24 hrs at room temperature and was then paraffin embedded. The other piece was snap frozen for RNA and protein analysis.

Immunohistochemistry

For immunohistochemical analysis tumors were dissected, fixed for 48 h in 4% PFA and then processed for paraffin embedding (Thermo Scientific Excelsior™ AS Tissue Processor and HistoStar™ Embedding Workstation). Samples were then sectioned at 5 µm, mounted on Superfrost™ Plus Adhesion Slides (Thermo Scientific) and immunostained for K167 (1/200, Thermo Scientific # RM-9106-20 S, clone SP6, rabbit monoclonal) and Cleaved CASPASE-3 (1/300, Cell Signalling Technology, Asp175, rabbit polyclonal) as briefly detailed below. Slides for immunohistochemistry were deparaffinized in xylene and then rehydrated in ethanol series (100%, 95%, and 70%) and distilled $H_2O$. Inhibition of endogenous peroxidase was achieved incubating the slides in 3% $H_2O_2$ for 15 min at RT. Epitope retrieval was performed in citrate buffer (pH6) using 2100 Retriever. Sections were blocked in 1% BSA solution for 40 min at RT and then incubated overnight at +4° C. with the primary antibody. For both the primary antibodies raised in rabbit, the EnVision+/HRP reagent (Dako K400311) was then applied on sections for 45 min at RT. Immunoreactivity was finally revealed via diaminobenzidinechromogen reaction (Peroxidase substrate kit, DAB, SK-4100; Vector Lab). Next, slides were counterstained in hematoxylin (Diapath # C0302), dehydrated in ethanol series, cleared in xylene, and permanently mounted with a resinous mounting medium (MicromountDiapath, #60200). A 0.1% Tween 20 TBS solution was used as washing buffer in between steps. To assess proliferative and apoptotic indexes, Ki67 or cleaved CASPASE-3 positive and negative nuclei were counted in three microscopic fields randomly selected from different regions of each tumor section applying a digital image analysis algorithm created on the ImageJ software platform. Proliferative and apoptotic indexes were then expressed as the ratio between positive and total number of nuclei.

Viability & Apoptosis Assays

CellTiter-Glo kit (Promega) or CellTiter 96 AQueous One Solution Cell Proliferation Assay (Promega) were used as cell viability assays. Cells were trypsinized, counted and seeded (5000 cells/well) in clear flat bottom 96 well plates (Corning). After 48/72 h cells were incubated with CellTiter-Glo or CellTiter 96 Aqueous One Solution as described in the manufacturer protocol.

After 1 h the luminescence/absorbance were read with Tecan Safire2 microplate reader. Caspase-Glo 3/7 Assay kit (Promega) was used as apoptosis assay. Cells were trypsinized, counted and seeded (5000 cells/well) in opaque flat bottom 96 well plates (Corning). After 48/72 h cells were incubated with Caspase-Glo 3/7 Assay as described in the manufacturer protocol.

Transfection of ASOs In Vitro

ASOs were transfected at a final concentration of 50 nM. Lipofectamine 2000 (Invitrogen) was used for PC3, . . . , HiPerfect (Qiagen) was used for PREC cells and electroporation with the Neon Transfection System (Invitrogen) was used for all the lymphoma cell lines. All reagents were used according to the manufacturer's protocol, with optimization for each cell line.

RNA Isolation and cDNA Synthesis

RNA was isolated using Purelink RNA Mini Kit (Thermo Fisher), with on column DNase digestion, according to the manufacturer's protocol. The RNA was reverse transcribed to cDNA using Maxima First Strand cDNA kit (Thermo Fisher).

Tamoxifen Injections 2-month-old CreER; and PRDM15$^{F/F}$;CreER or 5-week-old CreER;Eµ-Myc and PRDM15$^{F/F}$;CreER;Eµ-Myc mice were injected intraperitoneally for 3 consecutive days with 1.5 mg Tamoxifen (Sigma) in mineral oil.

DNA Isolation and Verification of Recombination

DNA was isolated from whole organs or cells in vitro with DNeasy Blood and Tissue Kit (Qiagen), according to the manufacturer's instructions. The following primers were used: F-5'-AAGACATTGGGTGCACAG-3' (SEQ ID NO: 96) & R-5'-GTGGCAGATGGCGCGGCAACACCATT-3' (SEQ ID NO: 97). PCR cycling conditions are as follows: initial holding temperature of 95° C. for 5 minutes, 37 cycles of denaturation (95° C. for 45 s), annealing (57° C. for 30 s)

and elongation (72° C. for 2 min). Lastly, an elongation temperature of 72° C. for 4 minutes and 4° C. holding temperature. DreamTaq Green PCR Master Mix (Thermo Fisher) was used, and the products were visualized by gel electrophoresis on a 2% agarose gel. For a recombined allele, a 500 bp band is expected. For an un-recombined allele, a band at around 1400 bp is expected.

Validation of ASO Efficacy by Semi-Quantitative PCR

The following primers were used: PRDM15 exon 11-13: F-5'-CAGTGCCCGAGAGCGAGAAT-3' (SEQ ID NO: 98) & R: 5'-TTGTGCTCCCCGAGCTGTTT-3' (SEQ ID NO: 99); PRDM15 exon 14-16: F-5'-TTGAGTCCAG-GAGGGTCGCC-3' (SEQ ID NO: 100) & R: 5'-CACTT-TACACGCCCACTGGCT-3' (SEQ ID NO: 101). PCR cycling conditions are as follows: initial holding temperature of 95° C. for 5 minutes, 27 cycles of denaturation (95° C. for 45 s), annealing (58° C. for 30 s) and elongation (72° C. for 1 min). Lastly, an elongation temperature of 72° C. for 4 minutes and 4° C. holding temperature. DreamTaq Green PCR Master Mix (Thermo Fisher) was used, and the products were visualized by gel electrophoresis on a 2% agarose gel. For PRDM15 exon 11-13, the expected product size is 371 bp and for PRDM15 11-13 with exon 12 skipped, the expected product size is 119 bp. For the full PRDM15 exon 14-16, the expected product size is 358 bp and for PRDM15 exon 14-16 with exon 15 skipped, the expected product size is 229 bp.

For quantitative real time PCR quantification of PRDM15 exon 15, the following primers were used: F: 5'-CCTCCG-GATGAGCCTGTGAGT-3' (SEQ ID NO: 102) & R: 5'-GGTGGCCAGCTTCCCCAGAAC-3' (SEQ ID NO: 103). Express SYBR GreenER qPCR Supermix (Thermo Fisher) was used according to the manufacturer's protocol.

Western Blotting

Total protein lysates were quantified with Bio-Rad RC DC protein assay. Equal amounts of protein were separated on 8% SDS-PAGE gels, and transferred to PVDF membranes. Transfer efficiency was validated with Ponceau S (Sigma P7170). The membranes were blocked in 5% milk in PBST, and incubated with primary antibodies against PRDM15 (1:500), Actin (1:1000, Santa Cruz 47778) or Prmt5 (1:500, Santa Cruz 22132) overnight. The following day, the membranes were washed thrice in PBST, incubated with the appropriate HRP-conjugated secondary antibody (1:10000, Goat (Promega V8051)/Mouse (Santa Cruz 2005)/Rabbit (Santa Cruz 2030) for 1 hour and washed thrice in PBST. The signals were visualized with Thermo Scientific Supersignal West Pico Chemiluminescent Substrate #34080 and film (Thermo Scientific CL-Xposure film #34089).

Whilst there has been described in the foregoing description preferred embodiments of the present invention, it will be understood by those skilled in the technology concerned that many variations or modifications in details of design or construction may be made without departing from the present invention.

REFERENCES

1 Fumasoni, I. et al. Family expansion and gene rearrangements contributed to the functional specialization of PRDM genes in vertebrates. BMC evolutionary biology 7, 187, doi:10.1186/1471-2148-7-187 (2007).

2 Ma, Z., Swigut, T., Valouev, A., Rada-Iglesias, A. & Wysocka, J. Sequence-specific regulator Prdm14 safeguards mouse ESCs from entering extraembryonic endoderm fates. Nat Struct Mol Biol 18, 120-127, doi:10.1038/nsmb.2000 (2011).

3 Yamaji, M. et al. PRDM14 ensures naive pluripotency through dual regulation of signalling and epigenetic pathways in mouse embryonic stem cells. Cell stem cell 12, 368-382, doi:10.1016/j.stem.2012.12.012 (2013).

4 Huang, S., Shao, G. & Liu, L. The PR domain of the Rb-binding zinc finger protein RIZ1 is a protein binding interface and is related to the SET domain functioning in chromatinmediated gene expression. J Biol Chem 273, 15933-15939 (1998).

5 Wu, H. et al. Structural biology of human H3K9 methyltransferases. PLoS One 5, e8570, doi:10.1371/journal.pone.0008570 (2010).

6 Hayashi, K., Yoshida, K. & Matsui, Y. A histone H3 methyltransferase controls epigenetic events required for meiotic prophase. Nature 438, 374-378, doi:DOI 10.1038/nature04112 (2005).

7 Koh-Stenta, X. et al. Characterisation of the histone methyltransferase PRDM9 utilising biochemical, biophysical and chemical biology techniques. The Biochemical journal, doi:10.1042/BJ20140374 (2014).

8 Eram, M. S. et al. Trimethylation of histone H3 lysine 36 by human methyltransferase PRDM9 protein. The Journal of biological chemistry 289, 12177-12188, doi:10.1074/jbc.M113.523183 (2014).

9 Derunes, C. et al. Characterization of the PR domain of RIZ1 histone methyltransferase. Biochem Bioph Res Co 333, 925-934, doi:10.1016/j.bbrc.2005.05.190 (2005).

10 Pinheiro, I. et al. Prdm3 and Prdm16 are H3K9me1 methyltransferases required for mammalian heterochromatin integrity. Cell 150, 948-960, doi:10.1016/j.cell.2012.06.048 (2012).

11 Eom, G. H. et al. Histone methyltransferase PRDM8 regulates mouse testis steroidogenesis. Biochem Bioph Res Co 388, 131-136, doi:10.1016/j.bbrc.2009.07.134 (2009).

12 Huang, S. The retinoblastoma protein-interacting zinc finger gene RIZ in 1p36-linked cancers. Front Biosci 4, D528-532 (1999).

13 Mock, B. A., Liu, L., LePaslier, D. & Huang, S. The B-lymphocyte maturation promoting transcription factor BLIMP1/PRDI-BF1 maps to D6S447 on human chromosome 6q21-q22.1 and the syntenic region of mouse chromosome 10. Genomics 37, 24-28 (1996).

14 Buyse, I. M., Takahashi, E. & Huang, S. Physical mapping of the retinoblastoma interacting zinc finger gene RIZ to D1S228 on chromosome 1p36. Genomics 34, 119-121, doi:DOI 10.1006/geno.1996.0249 (1996).

15 Yang, X. H. & Huang, S. PFM1 (PRDM4), a new member of the PR-domain family, maps to a tumor suppressor locus on human chromosome 12q23-q24.1. Genomics 61, 319-325, doi:DOI 10.1006/geno.1999.5967 (1999).

16 Pasqualucci, L. et al. Inactivation of the PRDM1/BLIMP1 gene in diffuse large B cell lymphoma. J Exp Med 203, 311-317, doi:10.1084/jem.20052204 (2006).

17 Nie, K. et al. MicroRNA-Mediated translation repression of PRDM1 in Hodgkin/Reed Sternberg cells—A potential pathogenetic lesion in Hodgkin lymphoma. Blood 108, 185a186a (2006).

18 Nie, K. et al. Epigenetic Down-Regulation of the Tumor Suppressor Gene PRDM1/Blimp1 in Diffuse Large B Cell Lymphomas A Potential Role of the MicroRNA Let-7. American Journal of Pathology 177, 1470-1479, doi:DOI 10.2353/ajpath.2010.091291 (2010).

19 Tam, W. et al. Mutational analysis of PRDM1 indicates a tumor-suppressor role in diffuse large B-cell lymphomas. Blood 107, 4090-4100, doi:DOI 10.1182/blood-2005-09-3778 (2006).
20 Mandelbaum, J. et al. BLIMP1 is a tumor suppressor gene frequently disrupted in activated B cell-like diffuse large B cell lymphoma. Cancer Cell 18, 568-579, doi: 10.1016/j.ccr.2010.10.030 (2010).
21 Hussin, J. et al. Rare allelic forms of PRDM9 associated with childhood leukemogenesis. Genome research 23, 419-430, doi:10.1101/gr.144188.112 (2013).
22 Woodward, E. L., Olsson, M. L., Johansson, B. & Paulsson, K. Allelic variants of PRDM9 associated with high hyperdiploid childhood acute lymphoblastic leukaemia. Br J Haematol 166, 947-949, doi:10.1111/bjh.12914 (2014).
23 Fog, C. K. et al. Loss of PRDM11 promotes MYC-driven lymphomagenesis. Blood 125, 1272-1281, doi:DOI 10.1182/blood-2014-03-560805 (2015).
24 Giallourakis, C. C. et al. Genome-wide Analysis of Immune System Genes by Expressed Sequence Tag Profiling. J Immunol 190, 5578-5587, doi:DOI 10.4049/jimmunol.1203471 (2013).
25 Skarnes, W. C. et al. A conditional knockout resource for the genome-wide study of mouse gene function. Nature 474, 337-342, doi:10.1038/nature10163 (2011).
26 Dewaele, M. et al. Antisense oligonucleotide-mediated MDM4 exon 6 skipping impairs tumor growth. J Clin Invest, doi:10.1172/JCI82534 (2015).
27 Koh, C. M. et al. MYC regulates the core pre-mRNA splicing machinery as an essential step in lymphomagenesis. Nature 523, 96-100, doi:10.1038/nature14351 (2015).
28 Hong, D. et al. AZD9150, a next-generation antisense oligonucleotide inhibitor of STAT3 with early evidence of clinical activity in lymphoma and lung cancer. Sci Transl Med 7,314ra185, doi:10.1126/scitranslmed.aac5272 (2015).

The invention claimed is:

1. A method of treating a cancer in a patient in need thereof, the method comprising administering to the patient an effective amount of an antisense oligonucleotide, wherein the oligonucleotide specifically hybridises to a target region of a PRDM15 pre-mRNA or mature mRNA, wherein the target region is any exon, intron or exon-intron boundary selected from exon 8, exon 9, exon 11, exon 12, exon 15, exon 16, exon 17, exon 18, exon 21, exon 24, exon 25, exon 29, intron 7, intron 8, intron 11, intron 14, and intron 15, wherein the method comprises determining the level of PRDM15 nucleic acid, protein or activity in a sample from the patient prior to administering the antisense oligonucleotide, and wherein the cancer is selected from B-cell lymphoma, liver cancer, glioblastoma, breast cancer, colon cancer, lung cancer, and prostate cancer.

2. A method of treating a cancer in a patient in need thereof, the method comprising administering to the patient an effective amount of an antisense oligonucleotide, wherein the antisense oligonucleotide comprises a sequence selected from any one of SEQ ID NOs: 1 to 73, and wherein the cancer is selected from B-cell lymphoma, liver cancer, glioblastoma, breast cancer, colon cancer, lung cancer, and prostate cancer.

3. The method according to claim 2, wherein the oligonucleotide is chemically linked to one or more conjugates that enhance the activity, cellular distribution, or cellular uptake of the antisense oligonucleotide.

4. The method of claim 2, wherein the cancer is B-cell lymphoma.

5. The method of claim 2, wherein the cancer is liver cancer.

6. The method of claim 2, wherein the cancer is glioblastoma.

7. The method of claim 2, wherein the cancer is breast cancer.

8. The method of claim 2, wherein the cancer is colon cancer.

9. The method of claim 2, wherein the cancer is lung cancer.

10. The method of claim 2, wherein the cancer is prostate cancer.

11. A method of treating a cancer in a patient in need thereof, the method comprising administering to the patient an effective amount of an antisense oligonucleotide, wherein the oligonucleotide specifically hybridises to a target region of a PRDM15 pre-mRNA or mature mRNA, wherein the target region is any exon, intron or exon-intron boundary selected from exon 8, exon 9, exon 11, exon 12, exon 15, exon 16, exon 17, exon 18, exon 21, exon 24, exon 25, exon 29, intron 7, intron 8, intron 11, intron 14, and intron 15, and wherein the cancer is a B-cell lymphoma.

12. The method according to claim 11, wherein the B-cell lymphoma is a follicular lymphoma or a diffuse large B-cell lymphoma.

* * * * *

SEQUENCE LISTING

<160> NUMBER OF SEQ ID NOS: 103

<210> SEQ ID NO 1
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1
augaucucuu cgcucccauc uucagccauc uc          32

<210> SEQ ID NO 2
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2
aacaugaucu cuucgcuccc aucuuca          27

<210> SEQ ID NO 3
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
auucggaguc gugguacugg cugcagucuu cacac          35

<210> SEQ ID NO 4
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4
ucgggacauu cggagucgug guacuggcug          30

```
<210> SEQ ID NO 5
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggcccagcuc gggacauucg gagucguggu a                                          31

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ccacugggcc cagcucggga cauucgg                                               27

<210> SEQ ID NO 7
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuuugaccau gaccacuggg cccagcucgg gacauu                                     36

<210> SEQ ID NO 8
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aucuuccagu cgucugaucu ccaaguuggg aggaagg                                    37

<210> SEQ ID NO 9
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
auuuggcgac ccuccuggac ucaaagggac cgaacugu                                   38

<210> SEQ ID NO 10
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cuccuggacu caaagggacc gaacuguguc cgcuuga                                    37
```

```
<210> SEQ ID NO 11
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
aaagggaccg aacuguqucc gcuugacgag cuga                                    34

<210> SEQ ID NO 12
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uccuuuuccc auuuggcgac ccuccuggac ucaaa                                   35

<210> SEQ ID NO 13
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guuggaggug ucgaagcaca cggggugccc guccuu                                  36

<210> SEQ ID NO 14
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
caucauccag uugcagucau ccucguugga ggugu                                   35

<210> SEQ ID NO 15
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
agucauccuc guuggaggug ucgaagcac                                          29

<210> SEQ ID NO 16
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gugcucggcc uccgccgcug gccgcaccag cauca                                   35

<210> SEQ ID NO 17
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
guucuggugc ucggccuccg ccgcu                                            25

<210> SEQ ID NO 18
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuggaggugu cgaagcacac ggggug                                           26

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ucauccaguu gcagucaucc ucguu                                            25

<210> SEQ ID NO 20
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
guugcacuca caggcucauc cggagggacc ucgguaauga u                          41

<210> SEQ ID NO 21
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uccggaggga ccucgguaau gaucucugcc acuugcu                               37

<210> SEQ ID NO 22
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucaucuggcg uugcacucac aggcucaucc ggaggga                               37

<210> SEQ ID NO 23
<211> LENGTH: 35
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
caugauccgc ucaucuggcg uugcacucac aggcu                              35

<210> SEQ ID NO 24
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uggugguggc cagcuucccc agaaccagcu ccaugauc                           38

<210> SEQ ID NO 25
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcuuccccag aaccagcucc augauccgcu cauc                               34

<210> SEQ ID NO 26
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
acucacaggc ucauccggag ggac                                          24

<210> SEQ ID NO 27
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ggaccucggu aaugaucucu gccacuugc                                     29

<210> SEQ ID NO 28
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gugauggugu uauucgaug augggugaac                                     30

<210> SEQ ID NO 29
<211> LENGTH: 38
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 29
uuaagcuccu cuugagcgug augguguuau ucugauga                          38

<210> SEQ ID NO 30
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uugcgccgga ugccgugucu gcuugagaga auuaagc                           37

<210> SEQ ID NO 31
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uguuugauga gcuugcgccg gaugccgugu cu                                32

<210> SEQ ID NO 32
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucucuuugcg gcugaacaau uuugcacacu cuucgcacuu                        40

<210> SEQ ID NO 33
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
acaauuuugc acacucuucg cacuuaaaca gcuugucac                         39

<210> SEQ ID NO 34
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uuaggcucuc uuugcggcug aacaauuuug cacacu                            36

<210> SEQ ID NO 35
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cgugcugcuu uaggcucucu uugcggcuga acaauuuu                           38

<210> SEQ ID NO 36
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cuuguaggaa acgugcugcu uuaggcucuc uuug                               34

<210> SEQ ID NO 37
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cucguuccug cugugcuugu aggaaacgug cugcuuuag                          39

<210> SEQ ID NO 38
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
aagugccgca gcgguaccug uacucgccgu c                                  31

<210> SEQ ID NO 39
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
gaaggucuuc ucacaagugc cgcagcggua ccuguacucg                         40

<210> SEQ ID NO 40
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ucgaugcgga aggucuucuc acaagugccg cag                                33

<210> SEQ ID NO 41
<211> LENGTH: 37
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 41
uggaacucca gcgcgcucuc gaugcggaag gucuucu                                37

<210> SEQ ID NO 42
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aguuguggaa cuccagcgcg cucucgaugc ggaagguc                               38

<210> SEQ ID NO 43
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uguccugcag uuguggaacu ccagcgcgcu cucgau                                 36

<210> SEQ ID NO 44
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccaccggccu ccagguccuc ucgcuucacu cgccgc                                 36

<210> SEQ ID NO 45
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gguucucccc accggccucc agguccucuc gcuucacu                               38

<210> SEQ ID NO 46
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cuucuuguaa cggaccaggu ucucccacc ggccuc                                  36

<210> SEQ ID NO 47
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 47
uguaacggac cagguucucc ccaccggccu ccaggu                                    36

<210> SEQ ID NO 48
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
aaggcuccuu cuuguaacgg accagguucu ccccaccg                                  38

<210> SEQ ID NO 49
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gcacccggaa ggcuccuucu uguaacggac cagguu                                    36

<210> SEQ ID NO 50
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
acacaccggg cacccggaag gcuccuucuu guaac                                     35

<210> SEQ ID NO 51
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cuugccacac accgggcacc cggaaggcuc cuucu                                     35

<210> SEQ ID NO 52
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
accgggcacc cggaaggcuc cuucuuguaa cggac                                     35

<210> SEQ ID NO 53
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uucagguacu ccuuccccg gccgaaggug ag                               32

<210> SEQ ID NO 54
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ucuccuugug caccuccaug augugcuuca gguacuccu                       39

<210> SEQ ID NO 55
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
cauagcccuu cuccuugugc accuccauga ug                              32

<210> SEQ ID NO 56
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
agugcaaagc gccgguugca gaugcugcag ccaua                           35

<210> SEQ ID NO 57
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
guagguggcc uucagugcaa agcgccggu                                  29

<210> SEQ ID NO 58
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ggaugaccau gugggcgugg uagguggccu ucagugc                         37

<210> SEQ ID NO 59
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 59
cccgcagauc ucgcaggggu ggaugu                                        26

<210> SEQ ID NO 60
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ggcgcuccag guucccgaug cuguugaaga uccgcccg                           38

<210> SEQ ID NO 61
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uguguggaug agcuugugge gcuccagguu cccgaug                            37

<210> SEQ ID NO 62
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uucuugucgc acacggagca cguccacugc uug                                33

<210> SEQ ID NO 63
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggucacguac uucuugucgc acacggagca cgucc                              35

<210> SEQ ID NO 64
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cgugcuucug cagcauguac ucggucacgu acuucuuguc                         40

<210> SEQ ID NO 65
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
```
cugaacgugc uucugcagca uguacucggu cacgu                                    35

<210> SEQ ID NO 66
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cuugucgugu gugagcugaa cgugcuucug c                                        31

<210> SEQ ID NO 67
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
cacagcuggc agcucugcgc cuccaccuug ucgugugu                                 38

<210> SEQ ID NO 68
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ugguggacac cuuggucccg cacagcuggc agcucu                                   36

<210> SEQ ID NO 69
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uaagcuccuc uugagcguga ugguguuau                                           29

<210> SEQ ID NO 70
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uugcggcuga acaauuuugc acacucuu                                            28

<210> SEQ ID NO 71
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uuuaggcucu cuuugcggcu gaacaauuu                                29

<210> SEQ ID NO 72
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
cacucuucgc acuuaaacag cuuguca                                  27

<210> SEQ ID NO 73
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uuguaggaaa cgugcugcuu uaggcucuc                                29

<210> SEQ ID NO 74
<211> LENGTH: 46
<212> TYPE: DNA
<213> ORGANISM: Homo sapiens

<400> SEQUENCE: 74
gtgtcagaga tggctgaaga tgggagcgaa gagatcatgt tcatct             46

<210> SEQ ID NO 75
<211> LENGTH: 94
<212> TYPE: DNA
<213> ORGANISM: Homo sapiens

<400> SEQUENCE: 75
ggtgtgaaga ctgcagccag taccacgact ccgaatgtcc cgagctgggc ccagtggtca    60
tggtcaaaga ctcctttgtg ttaagcaggg caag                               94

<210> SEQ ID NO 76
<211> LENGTH: 154
<212> TYPE: DNA
<213> ORGANISM: Homo sapiens

<400> SEQUENCE: 76
gtcatccctt cctcccaact tggagatcag acgactggaa gatggagccg aggggggtgtt   60 cgccatcact cagctcgtca agcggacaca gttcggtccc tttgagtcca ggagggtcgc   120
caaatgggaa aaggagtctg catttcccct gaag                              154

<210> SEQ ID NO 77
<211> LENGTH: 253
<212> TYPE: DNA
<213> ORGANISM: Homo sapiens

<400> SEQUENCE: 77
gtgttccaga aggacgggca ccccgtgtgc ttcgacacct ccaacgagga tgactgcaac    60
tggatgatgc tggtgcggcc agcggcggag gccgagcacc agaacctgac ggcctaccag   120
cacggcagcg acgtgtactt caccacctcc agagacatcc cccgggtac cgagctgcgc    180 gtgtggtatg cggccttcta tgccaagaag atggacaagc ccatgctgaa gcaggccggc   240

```
tctggcgtcc acg                                                        253
```

<210> SEQ ID NO 78
<211> LENGTH: 130
<212> TYPE: DNA
<213> ORGANISM: Homo sapiens
<400> SEQUENCE: 78

```
agcaagtggc agagatcatt accgaggtcc ctccggatga gcctgtgagt gcaacgccag     60
atgagcggat catggagctg gttctgggga agctggccac caccaccact gacaccagct   120
cggttccaaa                                                          130
```

<210> SEQ ID NO 79
<211> LENGTH: 182
<212> TYPE: DNA
<213> ORGANISM: Homo sapiens
<400> SEQUENCE: 79

```
gttcacccat catcagaata acaccatcac gctcaagagg agcttaattc tctcaagcag     60
acacggcatc cggcgcaagc tcatcaaaca gctcggggag cacaagcggg tttaccagtg   120
caatatctgc agcaagatct tccagaacag cagcaacctg agcaggcacg tgcgctcgca   180
tg                                                                  182
```

<210> SEQ ID NO 80
<211> LENGTH: 95
<212> TYPE: DNA
<213> ORGANISM: Homo sapiens
<400> SEQUENCE: 80

```
gtgacaagct gtttaagtgc gaagagtgtg caaaattgtt cagccgcaaa gagagcctaa     60
agcagcacgt ttcctacaag cacagcagga acgag                               95
```

<210> SEQ ID NO 81
<211> LENGTH: 88
<212> TYPE: DNA
<213> ORGANISM: Homo sapiens
<400> SEQUENCE: 81

```
gtggacggcg agtacaggta ccgctgcggc acttgtgaga agaccttccg catcgagagc     60
gcgctggagt tccacaactg caggacag                                       88
```

<210> SEQ ID NO 82
<211> LENGTH: 95
<212> TYPE: DNA
<213> ORGANISM: Homo sapiens
<400> SEQUENCE: 82

```
gagtgcggcg agtgaagcga gaggacctgg aggccggtgg ggagaacctg gtccgttaca     60
agaaggagcc ttccgggtgc ccggtgtgtg gcaag                               95
```

<210> SEQ ID NO 83
<211> LENGTH: 164
<212> TYPE: DNA
<213> ORGANISM: Homo sapiens
<400> SEQUENCE: 83

```
ctcaccttcg gccgggggaa ggagtacctg aagcacatca tggaggtgca caggagaag      60
```
ggctatggct gcagcatctg caaccggcgc tttgcactga aggccaccta ccacgcccac    120
atggtcatcc accgtgaaaa cctgccggac cccaacgtgc agaa                    164

<210> SEQ ID NO 84
<211> LENGTH: 80
<212> TYPE: DNA
<213> ORGANISM: Homo sapiens

<400> SEQUENCE: 84
gtacatccac ccctgcgaga tctgcgggcg gatcttcaac agcatcggga acctggagcg    60
ccacaagctc atccacacag                                                80

<210> SEQ ID NO 85
<211> LENGTH: 176
<212> TYPE: DNA
<213> ORGANISM: Homo sapiens

<400> SEQUENCE: 85
tgggcaagca gtggacgtgc tccgtgtgcg acaagaagta cgtgaccgag tacatgctgc    60
agaagcacgt tcagctcaca cacgacaagg tggaggcgca gagctgccag ctgtgcggga    120
ccaaggtgtc caccagggcc tccatagcc gacacatgcg gcgcaagcac cccgag         176

<210> SEQ ID NO 86
<211> LENGTH: 1190
<212> TYPE: DNA
<213> ORGANISM: Homo sapiens

<400> SEQUENCE: 86
gtgcgcacag ttggggattg ggggggggca gaggaggaat aatcatttgg tggcacatac    60
tgtgtgtatc tcactttatg ctcctcccaa actgcatgag gtgggtgttt ttatttccat   120
tttacagccc aggaatgtga ggcccagaa tgaacaatgt ctagatccac cctgtgaata   180
tatgtgtgtg gggggtgtca gtttatgctc atctacccac tatgcaagtg tttctggagg   240
tgaacctcaa ggatggatag ggaatagaat tattggatct gataacagct tatgtgggag   300
cacgagagtc ctccacaacg tcacgcattg atttagtccc cagagaagca agtgtttatg   360
gggcaccagg cataggttag gagtgagggg aaaaaaagtg acaaccggct ttttaaaaat   420
ggtgatatag gtgggcacga tggcttgtgc cataatccca gcactttggg aggctgaggt   480
aggaggattg cttgagccca gcaggtagag gctgcagtga gccttgatca caccactgca   540
ctccagcctg ggcgacagag caagaccctg tcaccaaaaa aaggtgatat atttgtttta   600
aaaatggaaa ttgatggcta atatgaaaag atgaaagtct gagttcatga ggccattcaa   660
atccattgct ttcattaaaa ataacattat ttgaggtgag aagatgtttc agggatccca   720
gccccatccc acaataagag gagacccac tgtgtgctct ctttagaaca ccacgtaatg   780
ttcctgtact ggctggagga ggcctttagt aggaattgtc tttaaacatt attttggtaa   840
gaggccaggc acggtggctc acacctgtaa tcccagcact tcagaggcc gaggcaggcg    900 gatcacaagg tcaagagatc gagaccagcc tggccaacat ggtgaaaccc cgtctctgct   960
aaaaatacaa aaattagctg ggtgtggtgg ctcacacctg tagtcccagc tactcaggag  1020
gctgaggcag gagaatcact tgaacctggg aggcagaggt tgcagtgagc caagatcctg  1080
ccactgtact ctatctatcc tgggcaacag agggagctca atttcaaaaa caaaacaaaa  1140 gtatttggt aagagcttgt cattaatgag gctctcttgt atcctgacag                1190

<210> SEQ ID NO 87
<211> LENGTH: 641
<212> TYPE: DNA
<213> ORGANISM: Homo sapiens

<400> SEQUENCE: 87

```
gtaagtgacc cagggacctg tcccaggtcc gagaccagcc ctatgtcata gaacacagat      60
gggcgtggcg cttgctgtct gggcaaagcc acgtctacat ttggttttta taatatagaa     120
aagctatata tttaaaattt ccctatgaaa catttattta ataagcagta cactacaggg     180
gtatggtttt aataggatca cctttctcag aactcctggc cgagggcact ttgcaggggg     240
tagcacttga ttcagaaaag taatccaggg ctaggcagga gggatgaacc tgctaacatt     300
ggccattttc atttatgctc attctttggg gagggtcttg gtcttcgtca ccatggaggt     360
gaccgtgctt gatttgaggc gtgcggcgga gctagagctt tccctggggg cgtgtcctgc     420
ctttgcactc ctcatgtgtg cacgagtgct gacagaggcc ttcgggacac aggccttctg     480
ccatccaatg caccctccct tgcttgtctt tgcagtgtcg gcatgcatgt gtctcatgac     540
tctgggtcac cctcatgggg ccagggtccc catttcccag gtttgtgttc tttaggtgtc     600
tccctccctg ggtgctctaa tgcccggatg tctgcttgca g                         641
```

<210> SEQ ID NO 88
<211> LENGTH: 2357
<212> TYPE: DNA
<213> ORGANISM: Homo sapiens

<400> SEQUENCE: 88

```
gtaaaggctg ttgccaaaca ggagctcagg aactgggtgt ttttctggcg ttcccatgtg      60
ggaatgggga gcaaggacca ctgagtttcc atgatttata aatgcctcaa aaacagctcc     120
aaatattgta ggtctgctta atttccaaga aaatgtttct ttttacattg caagagcatc     180
gatattaagt tagtattttg taattttcaa ttttgcagaa cactaaagag tgtgtttaag     240
acatatgcag gagaaaccca aatgctgact ccagctgtct tacgacctcc attgctgtcg     300
caggctttac gaggcagcgt cttgcagggg cccatcgctc tagttatttc cacacctgtg     360
cagagcgtat ggtagtttgc aaacctcttt caaagggaag gtgtttgttt aggcagtgat     420
gagacattgg gcaatagtgt gaagtttggc cgttctaaaa agcacatcag actgagagaa     480
gacagtggtt ctctactttg acgtgaactc gagaaaaacta gatgtatgt aaattgcaag     540
gcaggcttta gaataagtaa aaaatgagcc ctctggaagg ctatgaggcc aggcgaggct     600
ggttttgac tgttgccatg cctgccctct gtatcgtacc ccaagccagc cagtcttcag     660
aaatatctgt gaaataaaca aatgaggaat gggttgttag tcagcaaact tttcttagag     720
acccttgaaa tggatctgct tgtcttagga caggcagatg aagtcaacaa gcttgggttt     780
ttggaagtcc tttggaaagc tgagcttgta aggcagattt cagcaaaaag gggggaagaa     840
ggaaaggcac ttgatttgtt tacaaaagaa agaaggaagg aagggaggga gggaaggag      900
ggaaggaagg aagggagggg agggagggaa ggaaggaagg gaaggaaggg aggggaggga     960
gggaaggaag gaaaggaagg gagggagggg agggaggggaa ggaagggagg gagggagggg    1020
agggaaggaa ggaaaggaag ggaggaggg agggaggga aggaaggaaa ggaagggagg      1080
gaggggaggg aggaaggaa gggaggagg gggaggaggg aaggaaggaa aggaaggaag      1140
ggaggggagg gagggaggga aggaaggaa gaagggagg ggagggaggg agggaaggaa      1200
aggaaggaag ggagggaggg agggagggaa ggaaaggaag gaagggaggg agggagggag    1260
```

| | |
|---|---|
| ggaaggaaag gaaggaagga aggaaagaaa aggctgtttt aagttgaaga aatatgtaac | 1320 |
| aatgcttaaa acagcctcag aaaggccgtt ggctacctgc ctgtcctttg cagcacccat | 1380 |
| ccggtcgacg tacacagttg gtgtgggtgc acggttgggg gcgaggcccc tttaaagaag | 1440 |
| tcttttgtgc ccattttggt ggtccttcag ctacgcgatt ctgaaggtca tcgcctggta | 1500 |
| ctgggttgtt ctcagtgcat gcaccagcgt tcagctcctc tgtgcccacc agagagagcg | 1560 |
| tgccgccagc tgggagcaca ccttcctcag cagctggtgg tcattaggtg cctggtggtc | 1620 |
| ccccaccct gcctctcact tccaagggct ccgtctttgg agaggcctct ctaggagaag | 1680 |
| cttaggagag gggagagctc tcttcctgca gggaggaaga gaccatgaca tcagaaaata | 1740 |
| aggaacaaaa ccctcctata gtcatgtggt tgatttgaac ttcaaaatat gtaagttttt | 1800 |
| ctccctgctg cctgcctgca tttaatccat aaagcaatag tgctgtttga tagatgggga | 1860 |
| ggcagctcat aaagcctgag gagcccagca ccctgtggcg gagctgggag tagaactgtg | 1920 |
| tcccagttcc cagtgggcca tctggagagc cttaggtgtc cccgtgacac gtggactggg | 1980 |
| agtgaagctc aggtagctca aagcccacct ggaccaggac tagaactttg gtgtccccat | 2040 |
| gcccactaga acctgattag aacttgagtt ccgcacctgg gccgtgagta acactcaggt | 2100 |
| atcccaatga cacatagacc gctggctgtg tctgctgctt ccttttgcct gtgactaacc | 2160 |
| tgacccgtcc aaaccacatg gtctacctgt gaccctcctc actattgtaa acacctcaac | 2220 |
| atcccgtaca ggagcccta tggcctctga cgtggcactg tctagatggg ttcctcagca | 2280 |
| cctgcccccc acacgctgat acacagatgg gtaatcagcc atttccccgg cttctccatg | 2340 |
| ggccgactca ccttcag | 2357 |

<210> SEQ ID NO 89
<211> LENGTH: 7374
<212> TYPE: DNA
<213> ORGANISM: Homo sapiens

<400> SEQUENCE: 89

| | |
|---|---|
| gtatgtggcg gccccgatc cggagcccac cttcccttgt gcctcgccga aggggttatg | 60 |
| gtcccttggc tctgtgctga ccccacactg atgagatggg ttgggctggg ccagctgctg | 120 |
| ggatgcggag agtggaggag tggagagtcg ggtctgtctt tctgcttgtt ttaaacatcc | 180 |
| ttggtcagtt tgggcacgtg gatgtaacac aagttaacac agtgaggcag tgtttaacaa | 240 |
| cagagataca ttctcagaaa tgtgtcctgg ggcgatggca ttgtcatgag tgcatggtag | 300 |
| agcgcactct cgcgcacctt gatggcctgg cctgctacac acccaggctg tatggtgtag | 360 |
| cctgttctag ctaccagcct gtccagcatg tgactgtact gcatgctgtg ggcaactgta | 420 |
| acacatggtc agtatttgtc tatgtaaaca tagacaaagt aatagaggaa aaatactgta | 480 |
| ttagaatctc atgggaccac tgtctttgac tgaaaccttg tcacatggcg catgactgct | 540 |
| tagctctgcc ctgggggcta cgtgcagtga gtgacccatc ctcctaatcc tatgaggctg | 600 |
| gggtactagc cctgtctttg gacggaggaa acagcacaga gaggttaagg aactgacccc | 660 |
| aggtcacagt ggagtagatg aagaaatcag gattggtcca tggcacccgg ctccagtgtt | 720 |
| gctgctcacc gtgcaatggc ctcctcccag atttgggggc agtgtgtgtg tgcgcgcgtg | 780 |
| tgcatacctg tgtgtgtgtg catgcgtgtt caaagaaagc cctagtgaag gttatgtgcg | 840 |
| tgatctgccc aaatctagca ttcctgctga aaaagcgggt cacagtgcct gtcctgctaa | 900 |
| gccggggtca gggcatcact ttgccccatca agcggggctg ctgaattta aatctttctc | 960 |
| atccatgtta tgggtctttt tgacatagat cctcctcata aaacctgaag aaactctatg | 1020 |

```
aaattcctgg tatttgatgt cttttgacct gcaaaacagc aatttcatat tgccgaagct    1080
gacactaccc aggggagcaa atgttattta atgttgccat gaagattctt tgctcaaggg    1140
ggcgaaatag atattgactc tcctgacccc cctcccaaat gacctgattc tcatacgagc    1200 attgttttcct tgtttttataa atgcagtgta atccaaaata ttagtagctc ggtagcttaa    1260
gattcttaac ttattggaag gttctggtct gtcctgtttg tcagtatgat tgaggctttg    1320
taaaatgccc ctggttgtcc ctaatcccag gtccacaatg ggctgtgtgg gagtgtcccg    1380
gcgctgcgct gcccccataa aacaccagca acccagtgcc ttcacgtcag aaatgtgcct    1440
cccgcagtgc tggaggccac acgcccacgg tcagggtgtc agcagggctg gtcccttctg    1500
ggcaccctga gggagaatct gtcccgggac tctccccaac ctctggtggt ggctggcaca    1560
gtagcctttt gtgtcccttg gcttatggct gtgttactcc agtctctgcc tgtcttctct    1620
cccatgtctc tgtgtcatct cttcataaga ccacccgtca ttggattcag gcctccccaa    1680
tccagcatga cctcaccttaa acttgatgac atctgcacac atcctctccc aaaggtggta    1740
ggtggatgtg aattttgggg agccactatt gaacccacta tgggccatgt gagggctggg    1800
tggagagggg ccgctgggga tgctgctggg gagggttggt gaggagccag gcggctccct    1860
ctggggcctg cagcggtggc ggcgtcctct tcggccaggt tggtaaagtg agctgagtgt    1920
actgggggct tcgcacccctt cgcagagaaa gactgtggct ttgtggggag atgtttaaga    1980
atgaaaagga caaaagaac ttggagaaac ccactgctct tcacccagct gctcctagcc    2040
ccaccctcgt ggctttgcca aaaccaggtg cctggcctgg cccagcacaa gggaggcccc    2100
tgtggtggtg cctgctgggt caggggccgt ttccaagtcc tgcgaggctg ggctctctga    2160
gcagagccca agtaactgtg atcttcggga cctgggctcc ttgtgtctgg aattcctgaa    2220
ggcctaggca gctggcagca cgtgtgccca cggccagccc agactgcagc cacgccgggg    2280
tttgggttct gagatgccgg ccttggccgt ttaccccctt gtcagcttgt atcctggggg    2340
atgccctcac caccctcaag gctaaggtca aagcaaaggt tgccacgcct tattggagct    2400
acaggtgttt cgtattcatt ttacctgctg gagaccctttc aatctggagc tgagtttgaa    2460
acaatagatt taaatgaagt cagcctggga ctgtggtgtc gaacagagtc gcctctgatt    2520
tcggagatcc tagggtaatt cccattcctc cctaaaacct ctcagaataa aaggacactt    2580
gtaataattc taccaggaca gtctgtgtaa atgggaacgt atggtcacct gagcatagct    2640
taaacctaaa caaggttttt aattggggaa ataaataaac aacttagtta ctcttagatt    2700
tcagaaatgc tttttaggat ggtcacttgt gtttggggac aaatggcaag cagttatttc    2760
tggagaggta gtgaacatgg cgattccact cactggctgg ttgggtcctt ccttcccttt    2820
ccttcccgag agagccccct gttgagctct ggcttggccc ttgaagtgct gccggctgcc    2880
ctggggaact ttccctgggg tccacctgct gattgttcaa atggcaagcc agcagccgcg    2940
tcaacacctg ctcctcacac acacgctgcc tgtcaccctc tgcagccgcg tcagcgcccc    3000
cgccacacac acactgcctc tcaccctctg ccacctatct ggctccttcc cctgagcccc    3060
tcctccctga ccctgccagg ggtccctctc gaggcacagt ggcgcttcta gagccctgcc    3120
cgcccaatgc acccagggcc caccagagtc tgagtgtgtg tcgagcacct cacccagctg    3180
aagctatgca ctggagccca acgctgcctg cgtctcagaa atgagtatct cgatagataa    3240
caagaccttc gaagagaggc tagaaacatc cagaaagctg gccgcttgcc cagttctcac    3300
tgttcagact ggatacgtga aggactggag ttctagggta actgcgtaat cccactcctg    3360
```

```
ctcagtgacg tgccctctgg ggtggacact cccagagaga acgctgctgc atggtgggag    3420
aaaaggaggc cttttgtgca ttgttgtacc tctggcccag tgggagtagg cagagtgatg    3480
tgagtggcct ccggggccat tggtgtgctc ctagaaccgt attggcagcc gacgaaccca    3540
ggaaccgtct tcctgtaaat tacttattgt ggtggccgag tctttcctgg tgagcgtgag    3600
agatcctaag actcagtgac ttaattctgt ctctttgatt tgctccaaac atgcatcttc    3660
gtgtagaaat cagtcagttt tgcagatcag tggcgccgtc ttctaaatac agagaaaact    3720
ttggttttgt actgaaggag cagtaacaca tcccttttaaa agtaacttat tattttttc    3780
tggtagtgga ttttactttt ctagttccat cttttttcttt ttttgtagtt ttttgagata    3840
gggtctggca ctgttgccca ggctggagtg cagtggcatg atcgtggctc actgcagccg    3900
ccctcgtggg ctcaagtgat cctcccacct cagcctccct agtagctggg accacaggga    3960
tgtgccacca cacccagcta atttttttaa tttttatttt tagtagagat gggtctcact    4020
gtgttgccta ggctggtctt gaactcatgg attcgggcaa tcctcccacc ttccgaagtg    4080
ctgggattcc aggcgtgaag cactgtgcct ggccttaact tgttcttgag ctcacattaa    4140
gattgatttt gtttctttac aagaacctga acctgctgac agatggaggg ggcagccgaa    4200
gaaacatcct ggatcttcat gggagagagc atgaggccca ggaggagagt gttgggggg    4260
caccaggagg aaagtgtggg ggggcaccat gccagcaggg cgttgttatg ggacatcccg    4320
tccccaccag cttctgttcc cttttagtct cgctctgaga atccgctgct tgaagaatcc    4380
cacaagatcg tggacgaatg gaaatcagag ccagagtccc atttctcact caccttctca    4440
aacacacatg ggttccaacg agaaaatttt caaaatcacc tttctggtga aaagagtaaa    4500
atacaaacac attttataac attggggaaa ctgttcagtc acatatagca tcactgttct    4560
aactcaactg ctgttgccat ttgattcgca tttttctagta ttttttatttt taatttcatt    4620
ttatttttttt gagacagagt cttgctgtgt cacccaggct ggaatgtggt ggcccaatct    4680
cagctcactg caacctctac ctcccggttc aagcaattct cttgcctcag cctccccagt    4740
agctgggatt acaggcatgt accatcatgc ccagctaatt ttttttatttt tagtagagat    4800
ggggttttgc catgttggcc aggctggtgt tgaactcctg acttgaagtg attcacctgc    4860
ctcaacctcc caaagtgctg ggattacagg catgagccac ctcactggcc cctgtatttt    4920
aaaaaccagc actgatgaca tatagtttac attcagtaag actcaacaat tttaagtgta    4980
cagttcagag actttttttt tttttaagt cagtctgtcg cccaggctgg agtgcagtgg    5040
tgtgatcttg gctcactgca acctccacct cccgagttcg agcaattctc atgcctcagc    5100
ctctcaagag ctgtaattac aggcgcatgc caccacgcct ggctaatttg tgcatttttt    5160
agtagagacg gcgttttgct atgttgccca ggctggtctt gagctcctgg cctcaggtaa    5220
tccacccatc tgggcctccc aaagcgctgg gattacaggc atgagccagt gttcccgcca    5280
gtttagagac ttttgagtgt ctacagttgt ataagcacca ccacagctga gttacagacc    5340
tcgacttcat cccaggaagt tctctcgtgc ggccctgcag tcagccgcgc ccactggaat    5400
gccaggctgt tgctgtgctg tagctttgc tgttcctttt ttgtttgttt gttttaaact    5460
ctgcattttt gcatagcgga gctctagctg cacctcccat cttactgctt acttttcttt    5520
gtgtgcacag tctggctcac cacatcttag gccttttcc tactgttact atctctggca    5580
tcactttaaa gctgtatgat gttagatttt gctgggacac ttctcttttg ttggatattt    5640
aagtgattgg cagtcaagaa ttgccttctg actgttaact aatatttttct tcttaagaat    5700
tcttatcttt tacaattact attcggaaaa ccctgagtgc ttctcttgat gagcgggcag    5760
```

```
tcgtcatgac aagttttttct agtcctcttt acctagcagc agagcgccaa gttgaggaga    5820
acccacactt gtggggtgt ggaggcttat tgctggagac aatggccac gtggattcga       5880
agaaattccc cttattcaga agtggtggct tccagctaac ctgggccctt gtcctctttt     5940
tctgaaactc acatgcgagt gttttttctct ctttggaacc cgtgtatgtt tgggaaggtg    6000
agtgggaaat gggaatttgg ctctgatttc catttgtcct tgatcttttg ggattcttca     6060
agcagcggat tctcagagag caagcgtaaa agggaacaga agctggtggg gatgggtgt      6120
cccagaaaaa tgccctgctg gcagggtgcc ccccacaccg ttttctgctc tttctttatt    6180
tttagtatga caaaaaattt catattgcat ttatgcctct ttcttcttgt tatcttatga     6240
aaactcagaa catgcatgca cagggtgata gcagtaacct atatctttt ccttcattca     6300
ttgcatcctt agtgctggtt ttggatatga aaagatacat gttttttct agtgctgaat     6360
gcatatgcag ttgtacttct ggattatttt tttaaagacc caggagtttg tctttgtgag    6420
tggcccctgg agtttgccgt gggtgatgaa cttcaatgca ggctgtatcg tgattagagt    6480
cgaagtgatg ggcaggggtc ctgccctggg ccagccccca gagctgccag acgaggtgta    6540
gagaaactgg cctgggccag atcatggtac actcacttaa aacgcctccc aattgtaggt    6600
tgcacaagag catcagtgac tttttttgtta aaaggtgcct gtagttctct ttatagccag    6660
gcttacaccg catgccatgt accccagct tagctctccc tccccagatt cctgtgtggc     6720
atggactgag ggatagaggt gcttcctggg atagcggccc cctacctcag gtgcctattt    6780
aaaattaagt tcaaacttag taaaattaaa cacttatttc ctggaacatg agccacatct    6840
ggttagtggc tgccttgctg gataccagct gtggagcacg tcagtcatcc acagaaagct    6900
ctgccggata gcgctgggcg ggagcagcag cccagccaca cacggggggcg ccactggctg   6960
gccgtttggg gttccactgt ctcttattct atgagccagt gagagatgag gaattacact    7020
tggttcttga ggaatgcact tttctcatga agtcatataa gggatgagcc tggtccctct   7080
ggactggctt cttggaggag ttctcagctc tgtgactggt gaccctgcag caggcgtgtc   7140
tctgtgctca gttgcctcat ctgtgaaaag gggacagtca cacgaccgta tcagccatgt    7200
gtgtaaagct ctgaaaatgg tgtctgtcat gtggagtgac cacaggcccg tctgctgccg    7260
tcatcactgt catcaccgcc ctcagcaca cacccctcct ccgctgcgcc gggattcatg     7320
gagacatatg agctgcttgg gggtcacctt tttctcctct catgtcttt gaag           7374

<210> SEQ ID NO 90
<211> LENGTH: 1559
<212> TYPE: DNA
<213> ORGANISM: Homo sapiens

<400> SEQUENCE: 90
gtgatgagcg ggtcccgggg atgagtgcct gcgtggggcg cagccctcct ggcgcccgag      60
ggctggcggg gcaggggca gagggcgggg cggaaaaact cagtgtagaa aggcctcgtg      120
gaaggtagac tctaagcccg tctgtttttc tctcaatcaa ctctagtaaa gtacaatttc     180
catgtaatac atgtcacact aaaaaggata cagggtgtga attttgacaa atggatacag     240
ctgtgaaacc agcaccccccg tcagggtaga ggacatttct gtctcgttag ccactttcct    300
gactgtcttc tgtacgagtt cattccaccc atcctggaat ttctcacgaa tggactctgt    360
ctgcctcctt caggcagctt acagcctcga gacccgccca cgtggtttat ctgtggctcc    420
ttctcctgga ttgctgaaca gtgcttggtc catcacctgt gggtgggcac tgagttgctc    480
```

| | |
|---|---:|
| ccaggacctg tctagggctc atcctttgat tgtgcagtat cctcagttgg gtttgaagag | 540 |
| gcatttgacc ctcttccagg gtgtgtggtc tctgtaaggc tcttgtccct gtggtcctca | 600 |
| cacagccccc atccaagcca cctgcagcac acgcctcgtg ggcctcacag tgaggatgag | 660 |
| atctgatgct cagccactgg ccccttcaca tttgttactg acactgggca gtttttcttt | 720 |
| ttactgtctg ggatacacca ggatttcttt tatgagagtg aaaaggagtc cttattgctt | 780 |
| ctattaatta gagacaattg ggaagagcag ccattgtgga atattctgag cctccccttt | 840 |
| tctgctgtgg gtctgcagct tctaggctgt gcactgttgg gcgctgattt aggagcgcct | 900 |
| gaaagccccc tggccagttt ccccaggtct ctgtgaatag cagagaaga tgggggcggg | 960 |
| ggaaagcgtg tcaggtagat atttcactaa ttcttacttg tgttgagaag acatttagta | 1020 |
| ggcaaagtgg tagaaaccag tggttgaatt ttttttgtgta atcttcccct atttcattta | 1080 |
| tcttgggttt ctggccaggg tctccagtat tggcgatgat gtgatcttta actcttatac | 1140 |
| aaaatggtta gctaaaatgg ttttactaat gttggcacat ttaattagaa acattaacat | 1200 |
| ttctaaaact ctgtcagaat tgatgtagta agttcgaagt tctgctata tatccaaaat | 1260 |
| gttttttggtt ggtatgaaga gggattgaag taatgttatg atgttgtggt ttttaaaaag | 1320 |
| aataacaaat tataacttca gtttaggcta agaaaaacat tttgcttttc tgtttgtact | 1380 |
| agtaaatgtg tggatcccaa aatattgaca gttttttttt tccctctgt aaacctcaac | 1440 |
| atttgtgcct accattctgg cctggctgtg gttcccatgg ggcagtgtgt caccatggtt | 1500 |
| tgactgtgtt tgtcccctgc tcttgtggtt acttagcttg tcacatcccc ttcgtacag | 1559 |

<210> SEQ ID NO 91
<211> LENGTH: 1284
<212> TYPE: DNA
<213> ORGANISM: Homo sapiens

<400> SEQUENCE: 91

| | |
|---|---:|
| gtaagtcctg cctggcacct ggggccgtcc tgtggacaga caatgctggc agcagccagg | 60 |
| ccattctgga gggaaggcac cttcccagca ggaaagcccc agggaaggag atggaaacag | 120 |
| acctgctgag gaggcagcag gaatgttctg gagctcagga atgttctgga gctcaggagt | 180 |
| ttaatggtgc atccactgtg aaaacagctt tagaaaaatg ctttattttg gttaaatatg | 240 |
| cataaattta accatttaaa ccatgtttaa gtgcacaatt tagtggcatt caggatgttc | 300 |
| acactgttgg gcaatcatct cccccatcca tctgtggaac tttcccgtct tcccaagctg | 360 |
| aaacgctgtc cgcactaagc acccgctcca gccccctccc ccagccctg gcacccacca | 420 |
| ttctactttc tgtctctgtg gatttgatga ctctagagat gtcttataag tggaatcaga | 480 |
| caggatttgt ccttatgtga ctggcttatt ctaccccggc tcatccatgt gtagcctgtg | 540 |
| tcagaatttc cttcaacact gagtaatata ccatcatgca tatgccccat attttgtgtt | 600 |
| tccatgcatc cattgatgga cagttgggtt gcttctagct ttcgtgacgc tgctgtggta | 660 |
| aaatactttg ctatttgaat ttcagtaaat ataacagctt gccctgtgtt ttagttacga | 720 |
| ttcttgggtc atttttacca tggagttgag taagttggtg gtcacttctt tttggccctt | 780 |
| ttcggatcac ctcttatagt tggcaaaagt aatatcagaa atgatgttac ctgtttattt | 840 |
| atttatactt tatcttattg cccagaagag ttcaggtggc ttaccatcaa aaatacattt | 900 |
| aacagggaaa agaagttttg aaaatcaggt tcagataata tgtaaaacag agaagagtta | 960 |
| agacagagtg acaggagcag aaaacaggtg tggttattct aattgaggca caaattgacc | 1020 |
| tccaggcttt ctggtggcca gagttagaac agagtcaggt gtgtggctgt tgcagctaaa | 1080 |

```
gctgcctaat gtcattatat attcaaggtg tccctttcag atgccctgga agctgggagt    1140
gacgcccggg cgcattccct cctttctcgc atacaggctc gggattagct gggaagtttt    1200
ggaaggaggc cgttttcatg ctgcttgtaa cctggaactt ttttcccacc tgtcttttcc    1260
caacttattg acgtccctgg gcag                                           1284

<210> SEQ ID NO 92
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(26)
<223> OTHER INFORMATION: Phosphorothioate linkage
<220> FEATURE:
<221> NAME/KEY: modified_base
<222> LOCATION: (1)..(26)
<223> OTHER INFORMATION: 2'O-Methyl-modified nucleotide

<400> SEQUENCE: 92
uuggaggugu cgaagcacac ggggug                                         26

<210> SEQ ID NO 93
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: Phosphorothioate linkage
<220> FEATURE:
<221> NAME/KEY: modified_base
<222> LOCATION: (1)..(25)
<223> OTHER INFORMATION: 2'O-Methyl-modified nucleotide

<400> SEQUENCE: 93
ucauccaguu gcagucaucc ucguu                                          25

<210> SEQ ID NO 94
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(24)
<223> OTHER INFORMATION: Phosphorothioate linkage
<220> FEATURE:
<221> NAME/KEY: modified_base
<222> LOCATION: (1)..(24)
<223> OTHER INFORMATION: 2'O-Methyl-modified nucleotide

<400> SEQUENCE: 94
acucacaggc ucauccggag ggac                                           24

<210> SEQ ID NO 95
<211> LENGTH: 29
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: misc_feature
<222> LOCATION: (1)..(29)
<223> OTHER INFORMATION: Phosphorothioate linkage
<220> FEATURE:
<221> NAME/KEY: modified_base
<222> LOCATION: (1)..(29)
<223> OTHER INFORMATION: 2'O-Methyl-modified nucleotide

<400> SEQUENCE: 95
ggaccucggu aaugaucucu gccacuugc                                    29

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aagacattgg gtgcacag                                                18

<210> SEQ ID NO 97
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gtggcagatg gcgcggcaac accatt                                       26

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cagtgcccga gagcgagaat                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttgtgctccc cgagctgttt                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ttgagtccag gagggtcgcc                                              20
```

```
<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cactttacac gcccactggc t                                          21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cctccggatg agcctgtgag t                                          21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ggtggccagc ttccccagaa c                                          21
```